US006210708B1

(12) United States Patent
Walti et al.

(10) Patent No.: US 6,210,708 B1
(45) Date of Patent: Apr. 3, 2001

(54) CATIONIC VIROSOMES AS TRANSFER SYSTEM FOR GENETIC MATERIAL

(75) Inventors: Ernst Rudolf Walti, Munchenbuchsee; Reinhard Gluck, Spiegel bei Bern; Peter Klein, Langenbruck, all of (CH)

(73) Assignee: Nika Health Products Limited, Vaduz (LI)

( * ) Notice: Subject to any disclaimer, the term of this patent is extended or adjusted under 35 U.S.C. 154(b) by 0 days.

(21) Appl. No.: 09/414,872

(22) Filed: Oct. 8, 1999

Related U.S. Application Data

(63) Continuation-in-part of application No. 09/171,882, filed as application No. PCT/EP97/02268 on May 4, 1997.

(30) Foreign Application Priority Data

May 8, 1996 (EP) ..................... 96107282

(51) Int. Cl.[7] ..................... A61K 9/127; C12N 15/85
(52) U.S. Cl. ..................... 424/450; 435/458
(58) Field of Search ..................... 435/455; 424/450; 11/11

(56) References Cited

U.S. PATENT DOCUMENTS 4,261,975 4/1981 Fullerton et al. .................... 424/450

FOREIGN PATENT DOCUMENTS 0 497 997 A1 8/1992 (EP) .
WO 91/16024 10/1991 (WO) .
WO 92/13525 * 8/1992 (WO) .
WO 92/19267 11/1992 (WO) .
WO 93/14744 8/1993 (WO) .
WO 95/02698 1/1995 (WO) .
WO 95/30330 11/1995 (WO) .
WO 95/32706 12/1995 (WO) .
WO 96/14831 5/1996 (WO) .

OTHER PUBLICATIONS

Sizer, Philip J. H., et al. "Functional Reconstitution of the Integral Membrane Proteins of Influenza Virus into Phospholipid Liposomes", *Biochemistry* 1987, 26, pp. 5106–5113.

Vainstein, A., et al. "Fusogenic Reconstituted Sendai Virus Envelopes as a Vehicle for Instroducing DNA into Viable Mammalian Cells", *Methods in Enzymology*, vol. 101, 1983, pp. 492–513.

Yang, Yiping, et al. "Cellular Immunity to Viral Antigens Limits El–Deleted Adenoviruses for Gene Therapy", *Proc. Natl Acad. Sci. USA*, vol. 91, May 1994, pp. 4407–4411.

Morishita, Ryuichi, et al. "Enhanced Effectiveness of Antisense Oligonucleotides in Vascular Smooth Muscle Cells (VSMC) by HVJ Mediated Gene Transfer", *J. Cell. Biochem.*, 1993, 17E, pp. 239.

Stegmann, Toon, et al. "Functional Reconsitution of Influenza Virus Envelopes", *The EMBO Journal*, vol. 6, No. 9, 1987, pp. 2651–2659.

Martin, Francis J., et al. "Irreversable Coupling of Immunoglobulin Fragments to Preformed Vesicles: An Improved Method for Liposome Targeting", *The Journal of Biological Chemistry*, vol. 257, No. 1, Jan. 10, 1982, pp. 286–288.

(List continued on next page.)

*Primary Examiner*—Robert A. Schwartzman
*Assistant Examiner*—Katharine F Davis
(74) *Attorney, Agent, or Firm*—Oliff & Berridge, PLC

(57) ABSTRACT

The present invention relates to a positively charged virosome for efficient delivery of genetic material to resting or proliferating mammalian cells in vitro and in vivo. The virosome membrane contains cationic and/or polycationic lipids, at least one viral fusion peptide and preferably at least one cell-specific marker, advantageously selected from the group consisting of monoclonal antibodies, antibody fragments $F(ab')_2$ and Fab', cytokines, and growth factors, for a selective detection and binding of target cells. The invention further relates to a method for the manufacture of the novel virosomes and to applications thereof, particularly for the manufacture of pharmaceutical compositions to treat cancer or leukemia.

41 Claims, 20 Drawing Sheets

OTHER PUBLICATIONS

Felgner, Philip L., et al. "Lipofection: A Highly Efficient, Lipid–Mediated DNA–Transfection Procedure", *Proc. Natl Acad. Sci. USA*, vol. 84, Nov. 1987, pp. 7413–7417.

Ruysschaert, Jean–Marie, et al. "A Novel Cationic Amphiphile for Transfection of Mammalian Cells", *Biochemical and Biophysical Research Communications*, vol. 203, No. 3, 1994, pp. 1622–1628.

Behr, Jean–Paul, et al. "Efficient Gene Transfer into Mammalian Primary Endocrine Cells with Lipopolyamine–Coated DNA", *Proc. Natl. Acad. Sci. USA*, vol. 86, Sep. 1989, pp. 6982–6986.

Hoekstra, Dick, et al. "Fluorescence Method for Measuring the Kinetics of Fusion Between Biological Membranes", *Biochemistry*, 1984, 23, pp. 5675–5681.

Luscher–Mattli, M., et al. "A Comparative Study of the Effect of Dextran Sulfate on the Fusion and the In Vitro Replication of Influenza A and B, Semliki Forest, Vesicular Stomatitis, Rabies, Sendai, and Mumps Virus", *Archives of Virology*, 130, 1993, pp. 317–326.

Skehel, John J., et al "The Polypeptide Composition of Influenza A Viruses", *Virology*, 44, 1971, pp. 396–408.

Moolten, Frederick L. "Tumor Chemosensitivity Conferred by Inserted Herpes Thymidine Kinase Genes: Paradigm for a Prospective Cancer Control Strategy", *Cancer Research*, 46, Oct. 1986, pp. 5276–5281.

Tepper, Robert, I., et al. "Murine Interleuken–4 Displays Potent Anti–Tumor Activity in Vivo", *Cell*, vol. 57, May 5, 1989, pp. 503–512.

Townsend, Sarah E., et al. "Tumor Rejection after Direct Costimulation of CD8+T Cells by B7–Transfected Melanoma Cells", *Science*, vol. 259, Jan. 15, 1993, pp. 368–370.

Plautz, Gregory E., et al. "Immunotherapy of Maliganacy by In Vivo Gene Transfer into Tumors", Proc. Natl. Acad. Sci. USA, vol. 90, May 1993, pp. 4645–4649.

Chen, Phang–Lang, et al. "Genetic Mechanisms of Tumor Suppression by the Human p53 Gene", Science, vol. 250, Dec. 14, 1990, pp. 1576–1580.

Szczylik, Cezary, et al. "Selective Inhibition of Leukemia Cell Proliferation by BCR–ABL Antisense Oligodeoxynucleotides", Science, vol. 253, Aug. 2, 1991, pp. 562–565.

Calabretta, Bruno, et al. "Normal and Leukemic Hematopoietic Cells Manifest Differential Sensitivity to Inhibitory Effects of c–myb Antisense Oligodeoxynucleotides: An In Vitro Study Relevant to Bone Marrow Purging", Proc. Natl. Acad. Sci. USA, vol. 88, Mar. 1991, pp. 2351–2355.

Stegmann et al., Biochemistry 24: 3107–3113, Kinetics of pH–dependent fusion between influenza virus and liposomes, 1985.*

Verma et al., Nature 389: 239–242, Gene therapy—promises, problems, and prospects, Sep. 1997.*

Anderson, Nature 392: 25–30, Human gene therapy, Apr. 1998.*

* cited by examiner

Influence of time transfection on the amount of uptaken DNA-plasmid. $5x10^5$ cells of human, transformed primary embryonal kidney cell line 293 T were transfected with DOSPER- virosomes and DOSPER-liposomes containing $^3$H-labeled plasmid pGreen Lantern.

Influence of time transfection on the amount of uptaken DNA-plasmid. $5x10^5$ cells of monkey fibroblast cell line COS-1 were transfected with DOSPER- virosomes and DOSPER-liposomes containing $^3H$-labeled plasmid pGreen Lantern.

Influence of time transfection on the amount of uptaken DNA-plasmid. $5x10^5$ cells of human epithelioid carcinoma cell line HeLa were transfected with DOSPER- virosomes and DOSPER-liposomes containing $^3H$-labeled plasmid pGreen Lantern.

Influence of time transfection on the amount of uptaken DNA-plasmid. $5x10^5$ cells of mouse fibroblast cell line NIH3T3 were transfected with DOSPER- virosomes and DOSPER-liposomes containing $^3H$-labeled plasmid pGreen Lantern.

Influence of time transfection on the amount of uptaken DNA-plasmid. $5x10^5$ cells of human chronic myelogenous leukemia cell line K562 were transfected with DOSPER- virosomes and DOSPER-liposomes containing $^3$H-labeled plasmid pGreen Lantern.

Influence of time transfection on the amount of uptaken DNA-plasmid. $5x10^5$ cells of mouse myeloma cell line P3 were transfected with DOSPER- virosomes and DOSPER-liposomes containing $^3H$-labeled plasmid pGreen Lantern.

Influence of time transfection on the amount of uptaken DNA-plasmid. $5x10^5$ cells of human epithelioid carcinoma cell line HeLa were transfected with DOSPER-virosomes and DOTAP-virosomes containing $^3H$-labeled plasmid pGreen Lantern.

Influence of time transfection on the amount of uptaken DNA-plasmid. $5 \times 10^5$ cells of human chronic myelogenous leukemia cell line K562 were transfected with DOSPER- virosomes and DOTAP-virosomes containing $^3H$-labeled plasmid pGreen Lantern.

SEQUENCE LISTING

```
<160> NUMBER OF SEQ ID NOS: 19

<210> SEQ ID NO 1
<211> LENGTH: 26
<212> TYPE: PRT
<213> ORGANISM: Artificial Sequence
```

-continued

<220> FEATURE:
<223> OTHER INFORMATION: Description of Artificial Sequence:
hemagglutinin-type fusogenic peptide

<400> SEQUENCE: 1

Cys Cys Cys Gly Leu Phe Gly Ala Ile Ala Gly Phe Ile Glu Asn Gly
1 5 10 15

Trp Glu Gly Met Ile Asp Gly Trp Tyr Gly
20 25

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence:
hemagglutinin-type fusogenic peptide

<400> SEQUENCE: 2

Gly Leu Phe Gly Ala Ile Ala Gly Phe Ile Glu Asn Gly Trp Glu Gly
1 5 10 15

Met Ile Asp Gly Trp Tyr Gly Cys Cys Cys
20 25

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence:
hemagglutinin-type fusogenic peptide

<400> SEQUENCE: 3

Cys Cys Cys Gly Leu Phe Gly Ala Ile Ala Gly Phe Ile Glu Asn Gly
1 5 10 15

Trp Glu Gly Met Ile Asp Gly
20

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence:
hemagglutinin-type fusogenic peptide

<400> SEQUENCE: 4

Gly Leu Phe Gly Ala Ile Ala Gly Phe Ile Glu Asn Gly Trp Glu Gly
1 5 10 15

Met Ile Asp Gly Cys Cys Cys
20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence:
hemagglutinin-type fusogenic peptide

<400> SEQUENCE: 5

Cys Cys Cys Gly Leu Phe Glu Ala Ile Ala Gly Phe Ile Glu Asn Gly
1 5 10 15

Trp Glu Gly Met Ile Asp Gly
20

-continued

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 6

```
Gly Leu Phe Glu Ala Ile Ala Gly Phe Ile Glu Asn Gly Trp Glu Gly
  1               5                  10                  15

Met Ile Asp Gly Cys Cys Cys
             20
```

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 7

```
Cys Cys Cys Glu Leu Phe Gly Ala Ile Ala Gly Phe Ile Glu Asn Gly
  1               5                  10                  15

Trp Glu Gly Met Ile Asp Gly
             20
```

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 8

```
Glu Leu Phe Gly Ala Ile Ala Gly Phe Ile Glu Asn Gly Trp Glu Gly
  1               5                  10                  15

Met Ile Asp Gly Cys Cys Cys
             20
```

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 9

```
Cys Cys Cys Leu Phe Gly Ala Ile Ala Gly Phe Ile Glu Asn Gly Trp
  1               5                  10                  15

Glu Gly Met Ile Asp Gly
             20
```

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 10

-continued

Leu Phe Gly Ala Ile Ala Gly Phe Ile Glu Asn Gly Trp Glu Gly Met
1 5 10 15

Ile Asp Gly Cys Cys Cys
20

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 11

Cys Cys Cys Pro Pro Gly Ala Val Ile Gly Thr Ile Ala Leu Gly Val
1 5 10 15

Ala Thr Ala Ala Gly Ile Thr
20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 12

Pro Pro Gly Ala Val Ile Gly Thr Ile Ala Leu Gly Val Ala Thr Ala
1 5 10 15

Ala Gly Ile Thr Cys Cys Cys
20

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 13

Cys Cys Cys Pro Ala Gly Val Val Ile Gly Leu Ala Ala Leu Gly Val
1 5 10 15

Ala Thr Ala Ala Gly Val Thr
20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: hemagglutinin-type fusogenic peptide

<400> SEQUENCE: 14

Pro Ala Gly Val Val Ile Gly Leu Ala Ala Leu Gly Val Ala Thr Ala
1 5 10 15

Ala Gly Val Thr Cys Cys Cys
20

<210> SEQ ID NO 15
<211> LENGTH: 23
<212> TYPE: PRT

-continued

```
<213> ORGANISM: Artificial Sequence
<220> FEATURE:
<223> OTHER INFORMATION: Description of Artificial Sequence:
      hemagglutinin-type fusogenic peptide

<400> SEQUENCE: 15

Cys Cys Cys Pro Ile Gly Ala Ile Ile Gly Gly Val Ala Leu Gly Val
  1               5                  10                  15

Ala Thr Ala Ala Gly Ile Thr
             20


<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence:
      hemagglutinin-type fusogenic peptide

<400> SEQUENCE: 16

Pro Ile Gly Ala Ile Ile Gly Gly Val Ala Leu Gly Val Ala Thr Ala
  1               5                  10                  15

Ala Gly Ile Thr Cys Cys Cys
             20


<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence:
      hemagglutinin-type fusogenic peptide

<400> SEQUENCE: 17

Gly Leu Phe Glu Ala Ile Ala Gly Phe Ile Glu Asn Gly Trp Glu Gly
  1               5                  10                  15

Met Ile Asp Cys
             20


<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: sense
      oligodeoxynucleotide of c-myb gene

<400> SEQUENCE: 18

gcccgaagac cccggcac                                                18


<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: antisense
      oligodeoxynucleotide of c-myb gene

<400> SEQUENCE: 19

tgtgccgggg tcttcgggc                                               19
```

CATIONIC VIROSOMES AS TRANSFER SYSTEM FOR GENETIC MATERIAL

This is a Continuation-in-Part of application Ser. No. 09/171,882 filed Dec. 30, 1998, which in turn is a U.S. National Stage of PCT/EP97/02268 filed May 4, 1997. The entire disclosures of the prior applications are hereby incorporated by reference herein in their entirety.

FIELD OF INVENTION

The present invention is in the field of gene biotechnology and gene therapy and relates to novel virosomes, i.e., positively charged liposomal vesicles containing viral glycoproteins in the membrane, for efficient transfer of genetic material to target locations, a method of manufacture and useful applications thereof. The present cationic virosomes are particularly suitable for the specific and unspecific, non-infectious delivery of genes to target cells in vitro and in vivo.

BACKGROUND OF THE INVENTION

Liposomes are widely used as carriers for drug delivery and as protective shelters for short-lived pharmaceutical substances or against (bio)chemical attack by bodily fluids. Liposomes containing reconstituted membrane proteins or parts thereof from viral envelopes are usually called "virosomes" (Sizer et al., Biochemistry 26:5106–5113, 1987). They have been applied for non-specific delivery of various drugs and DNA molecules (Vainstein et al., Methods Enzymol. 101:492–512, 1983). It turned out to be a major drawback that these virosomes fused with the cell membrane of the target cells resulting in an uncontrolled release of the transported material into the cytoplasm of the target cells where the unprotected material was readily attacked by degradative intracellular processes.

WO 92/13525, the whole contents of which shall herewith be incorporated by reference, reports that virosomes made of phospholipid bilayer membranes which are targeted with viral spike proteins from influenza virus and with cell-specific markers such as, e.g., monoclonal antibodies, very efficiently fuse with model membranes and animal cells due to a virus-like penetration mechanism by way of receptor-mediated endocytosis. While these virosomes are successfully applied to deliver chemical substances and desired drugs to target locations, they suffer from certain disadvantages with respect to stable incorporation and transfer of charged molecules such as, for instance, negatively charged nucleic acids.

Within the last few years the delivery, notably the cell-specific delivery, of genetic material incorporated in liposomes has gained more and more attention and importance, particularly with regard to applications in anti-cancer and gene therapy. Several methods are currently available for delivery of DNA or RNA to cells: Virus mediated methods, lipid mediated methods, and other methods like microinjection and electroporation. The advantages and disadvantages of current gene transfer techniques can be summarized as follows:

a) Virus mediated gene transfer: Genes can be introduced stably and efficiently into mammalian cells by means of retroviral vectors. However, the efficiency of gene transfer to non-replicating cells is very low because retroviruses infect only dividing cells. Further, general safety concerns are associated with the use of retroviral vectors relating to, for instance, the possible activation of oncogenes. Replication-defective adenovirus has become the gene transfer vector-of-choice for a majority of investigators. The adenovirus vector mediated gene delivery involves either the insertion of the desired gene into deleted adenovirus particles or the formation of a complex between the DNA to be inserted and the viral coat of adenovirus by a transferring-polylysine bridge. The drawback of this very efficient system in vivo is an undefined risk of infection or inflammation: Despite the E1 gene deletion that renders the virus defective for replication, the remaining virus genome contains numerous open reading frames encoding viral proteins (Yang et al. 1994; Proc. Natl. Acad. Sci. USA 91, 4407–4411). Expression of viral proteins by transduced cells elicits both humoral and cellular immune responses in the animal and human body and thus, may provoke inflammation and proliferation.

In the HVJ (Sendai virus) mediated method the foreign DNA is complexed with liposomes. The liposomes are then loaded with inactivated Sendai virus (hemagglutinating virus of Japan; HVJ). This method has already been used for gene transfer in vivo to various tissues. In addition, cellular uptake of antisense oligonucleotides by HVJ-liposomes was reported (Morishita et al. 1993; J. Cell. Biochem. 17E, 239). A particular disadvantage is, however, that the HVJ-liposomes tend to non-specifically bind to red blood cells.

b) Lipid mediated gene transfer: Positively charged liposomes made of cationic lipids appear to be safe, easy to use and efficient for in vitro transfer of DNA and antisense oligonucleotides. The highly negatively charged nucleic acids interact spontaneously with cationic liposomes. Already by simple mixing of the polynucleotides with preformed cationic liposomes a complete formation of DNA-liposome complexes is achieved. However, due to the lack of fusion peptides and cell-specific markers on the liposomal membrane the in vivo transfection efficiency is very low and the incubation times are long, wherefore high doses have to be administered in order to achieve a desired effect. Consequently, undesired side-effects may occur since there is evidence that large amounts of cationic lipids can exhibit toxic effects in vivo.

Small oligonucleotides are currently being tested as therapeutic agents for the treatment of cancer and as antiviral agents. Only one of the two DNA strands is transcribed to synthesize messenger RNA (mRNA). The DNA strand transcribed into RNA is called the coding strand or sense strand. The complementary, non-coding or antisense strand has the same sequence as the mRNA. When the non-coding strand is transcribed, it produces antisense RNA molecules that are able to bind to target (sense) mRNA. Once the antisense RNA is bound to the sense RNA the resulting RNA duplex molecules cannot be translated and the production of the protein is blocked. Usually, short synthetic antisense oligonucleotides of 18 to 22 bases effectively bind to the mRNA and inhibit mRNA translation. By this mechanism antisense oligonucleotides can stop the proliferation of human cancer cells. Genes that are involved in cancer exert their effect through overexpression of their normal structural proteins. Genes such as c-fos, c-myc, L-myc, N-myc, c-myb, abl, bcr-abl, c-raf, c-erb-2, K-ras may be potential targets for antisense cancer therapy. Antisense oligonucleotides are also an attractive potential alterative to conventional drugs such as, for example, antiviral agents such as, e.g., the antisense oligonucleotides of tat and gag gene of the human immunodeficiency virus (HIV).

Liposomal membranes comprising reconstituted virus envelopes as described in the literature (Stegmann et al.; EMBO J. 6:2651–2659, 1987) may be called virosomes. They usually comprise a phospholipid bilayer containing phosphatidylcholine (PC) and phosphatidylethanolamine (PE) together with viral envelope, e.g., spike proteins embedded in the membrane. The conventional methods to incorporate genetic material into PC, PE-virosomes suffer from the drawback of a rather low efficiency of nucleic acid incorporation.

SUMMARY OF THE INVENTION

The present invention therefore relates to a novel cationic virosome which due to its specific membrane composition may very efficiently be loaded with any desired genetic material comprising long and short chain DNA or RNA, oligodeoxynucleotides, ribonucleotides, peptide nucleic acids (PNA), ribozymes (RNA molecules with enzymatic activities), genes, plasmids and vectors and, thus, convincingly overcomes the drawbacks of the prior art.

The invention further relates to a method for the efficient reconstitution of hemagglutinin of influenza virus A, particularly of strain A/Singapore, into substantially unilamellar cationic lipid vesicles resulting in the formation of cationic virosomes with a mean diameter of approximately 120–180 nm and a continuous lipid bilayer, which is substantially free from the disadvantage of leakage seen with many conventional virosome preparations. The structure of the—preferably unilamellar—cationic brayer membrane is such that the hydrophilic, positively charged heads of the lipids are oriented towards the aqueous phase(s) and the hydrophobic fatty acid tails are oriented towards the center of the bilayer. It could be shown by electron microscopy that the reconstituted viral spike proteins (hemagglutinin) are integrated in the lipid bilayer and extend from the surface of the cationic vesicles (FIG. 1).

DETAILED DESCRIPTION OF PREFERRED EMBODIMENTS

Figure 1:
FIG. 1 shows a micrograph of DOTAP virosomes with viral spike proteins.

The lipid composition of the vesicle membrane comprises cationic and/or polycationic lipids together with phosphatidylethanolamine and optionally other phospholipids such as phosphatidylcholine.

For most cases, it is advantageous to choose a lipid composition of the membrane comprising—based on total lipids—10% by weight or less, preferably 1–10%, of phosphatidylethanolamine together with 90% by weight or more, preferably 90–99%, of other lipids including the cationic and/or polycationic lipids, and optionally further including phosphatidylcholine. If present, phosphatidylcholine should be present in an amount of, for example, 5–50% by weight, based on total lipids.

The presence of phosphatidylethanolamine (PE) in the membrane is preferred for anchoring a cell-specific marker to the virosome by means of a bifunctional crosslinker. Where cell-specific targeting of the virosomes is not required (e.g., for application in defined cell cultures in vitro) or where the cell-specific marker is attached to the membrane other than by way of a bifunctional crosslinker, PE may optionally be absent from the virosome membrane.

In a preferred embodiment, the present invention also relates to the irreversible covalent linkage of cell-specific markers to the cationic virosomes including but not being limited to monoclonal antibodies, antibody fragments such as $F(ab')_2$ and Fab' fragments, cytokines, and/or growth factors, useful for a selective detection and binding of target cells. They are linked to the vesicle membrane such that they extend to the exterior and exert essentially full functional activity with respect to receptor detection and binding.

Coupling cell-specific markers such as antibody fragments to preformed vesicles as described by, e.g., Martin et al. (J. Biol. Chem. 257: 286–288, 1982) often leads to low and frequently irreproducible coupling yields—a complication that imposes a significant limitation to the targeting strategy. Therefore, according to a preferred embodiment of the present invention the markers are coupled to preformed phosphatidylethanolamine-crosslinker molecules such as, for example, N-[4-(p-maleimido-phenylbutyryl]-phosphatidylethanolamine (MPB.PE) in the presence of a detergent.

In order to achieve the best possible results it is advantageous to carefully isolate and purify the viral glycoproteins before reconstitution in order to avoid inactivation by either proteolytic digestion or reduction of intramolecular S—S bonds. Accordingly, it is preferred that the conjugated markers, e.g., marker-MPB.PE, be separated from unconjugated phosphatidylethanolamine-crosslinker molecules (e.g., MPB.PE) by affinity chromatography with an activated agarose matrix, preferably with reduced Thiopropyl Sepharose 6B. Aliquots of the purified conjugated markers (phosphatidylethanolamine-crosslinker-marker molecule complexes) are then added to the detergent solution containing the mixture of dissolved membrane lipids, fusion peptides and other desired ingredients, before the cationic virosomes are formed thereof.

It is advantageous to carry out the coupling procedure of the bifunctional crosslinker with the phospholipid and the cell-specific marker in a separate process prior to the preparation of the virosomes. This procedure allows to better control and optimize the surface density of the virosome membranes, particularly with respect to the number of cell-specific markers linked thereto. The improved control of the concentration of protein molecules embedded in or linked to the membrane is important in as much as an unbalanced ratio of fusion peptides (e.g., hemagglutinin) and cell-specific markers (e.g., antibody Fab' fragments) on the virosome membrane may reduce or even destroy their selective properties and—at the extreme—may result in clotting and precipitation of the vesicles.

The use of antibody fragments $F(ab')_2$ and Fab' instead of whole antibody molecules as cell-specific markers is particularly advantageous, because they are far less immunogenic than the whole antibody. Also, the absence of the Fc domain eliminates a range of undesired Fc-mediated biological and immunological activities such as, for example, complement activation via the classical pathway and acute humoral responses eventually resulting-amongst others—in the clearance of attached virosomes from the target cell surface via interaction between the antibody and its Fc-receptor on the target cell.

Unlike known liposomal compositions for delivery of nucleic acids, the present cationic virosomes usually need not fuse with or destabilize the plasma cell membrane to enter the cytoplasm. They are capable of entering the host cells via a two step mechanism: 1. attachment and 2. penetration. In the first step they bind via the fusion peptides (e.g. hemagglutinin) and/or the cell-specific markers to cell receptors, particularly to membrane glycoproteins or glycolipids with a terminal sialic acid, and are then very efficiently incorporated by receptor-mediated endocytosis. In case of virosomes bearing cell-specific markers, e.g., antibody fragments, these markers will additionally recognize antigenic structures on the target cell surface, resulting in an attachment by two different binding mechanisms. Thus, the present cell-specific virosomes exert a selectivity for various cell types owing to their cell-specific markers on the membrane and, simultaneously, a high capability for cell penetration by endocytosis owing to the viral fusion peptide, e.g., hemagglutinin. Virosomes with Fab' fragments that recognize tumor-associated antigens such as TAG72, CEA, 17-1A, CA 19-9 or leukemia-associated antigens such as CD10 (CALLA=Common Acute Lymphocytic Leukemia Antigen) and CD20 will bind selectively to tumor or leukemia cells carrying the mentioned antigens on their cell surface.

In the second step, when entering the host cells via receptor-mediated endocytosis the virosomes get entrapped in endosomes. Subsequently, the pH within the endosomes decreases to about pH 5–6, which activates the hemagglutinin fusion peptide and triggers the fusion of the virosomal membrane with the endosomal membrane. The membrane fusion reaction opens the lipid envelope of the virosomes and liberates the entrapped genetic material into the cytosol. This mechanism considerably improves the chances of the transferred genetic material to reach the nucleus before getting cleared by digestive degradation and/or exocytosis.

An objective of the present invention is to provide positively charged lipid vesicles comprising cationic or polycationic lipids and an internal—usually aqueous—space, and further comprising at least one viral fusion peptide embedded or integrated in or covalently linked to the vesicle membrane. The vesicle preferably also comprises at least one cell-specific marker on the membrane. It is a further object of the present invention to provide vesicles having full biological fusion activity, i.e., having essentially the same fusion activity as intact influenza virus. The fusion peptide is a viral-glycoprotein such as hemagglutinin or a derivative thereof, or a synthetic fusion peptide being capable of inducing a rapid fusion of said vesicles with the endosomal membranes of the target cells after endocytosis.

The novel vesicles or virosomes are particularly useful to transfer any desired genetic material to target locations, in particular to animal and human cells and tissues in vitro and in vivo. It is emphasized that the novel virosomes are not only able to penetrate proliferating, i.e., replicating cells but also non-proliferating, i.e., resting cells, which feature makes them widely applicable in the fields of biosciences, pharmacology and medicine, both as a research and/or diagnostic tool and as a medicament. For the use as a medicament, the present virosomes may be part of a pharmaceutical composition which further comprises usual additives and pharmaceutically suitable carriers. It is preferred that the pharmaceutical composition is prepared as an injection solution, but other forms of preparation, e.g., emulsions, cremes, gels, ointments, for topical or systemic administration may be advantageous for some applications.

Therefore, it is also an objective of the present invention to use the present virosomes for the manufacture of a pharmaceutical composition suitable for the prophylactic and/or therapeutic treatment of animal or human individuals who may benefit from such treatment. It is another objective of the present invention to use the present virosomes for the manufacture of a diagnostic kit for in vitro and in vivo applications.

In one embodiment the present vesicles are obtained by a process comprising an efficient reconstitution of hemagglutinin (HA) of influenza virus A. Accordingly, it is also an object of the present invention to teach a method of preparing cationic virosomes. In a preferred embodiment, the method further comprises the steps of incorporating genetic material into the cationic lipid vesicles. Basically, the method of preparation comprises the following steps:

1) Dissolution of the cationic lipids in a non-ionic detergent, preferably octaethyleneglycol mono-n-dodecylether (OEG, $C_{12}E_8$), together with—preferably purified—viral spike glycoproteins, genetic material desired or delivery and optionally preformed complex molecules made of phosphatidylethanolamine, crosslinker and cell-specific marker; and
2) vesicle formation through—preferably repeated—detergent removal with detergent absorbing micro-carrier beads, preferably polystyrene beads of the SM-2 Biobeads type with a preferred mesh size (wet) of 20–50 (0–84—0.30 mm).

In a preferred embodiment of the invention, a suitable bifunctional crosslinker is applied to link the cell-specific marker irreversibly to the vesicle membrane. The cell-specific marker, which is directed to a cell-receptor responsible for the selective binding of the virosome to the cell, is bound to the crosslinker in such a manner that it is still fully biologically active. It is preferred that the crosslinker be employed in the form of a preformed molecule-complex wherein the crosslinker is covalently bound to either phosphatidylethanolamine or to both phosphatidylethanolamine and a cell-specific marker.

Due to the functionally active fusion peptides of the present virosomes the encapsulated material is released to the cytosol of a target cell mainly upon decrease of the endosomal pH (as outlined above). Such controlled release on one hand prolongs the residence time of the delivered material within the target cell and on the other hand avoids an undesired long stay of the virosomes inside the endosomes and therewith reduces the danger of unspecific degradation of the valuable substances transported by the virosomes.

In still another embodiment, the present invention refers to vesicles where the membrane lipids additionally comprise phosphatidylcholine and phosphatidylethanolamine, which further improves the possibilities of specific virosome design and/or facilitates the anchoring of fusion peptides and/or cell-specific markers to the membrane.

The term "fusion peptide" refers to peptides or proteins capable of inducing and/or promoting a fusion reaction between the virosome membrane and a lipid membrane of the target cell. In most embodiments, it refers to viral spike glycoproteins containing the fusion peptide, particularly to the complete hemagglutinin trimer of viral surface spikes, a monomer thereof, or one or both cleaved subunits, the glycopeptides HA1 and HA2, containing the functional fusion peptide. In another embodiment of the present invention the term refers to the pure fusion peptide itself, either isolated from natural sources or synthetically produced. In a particularly preferred embodiment of the present invention, these polypeptides containing the fusion peptide refer to influenza hemagglutinins, especially the one of the A-$H_1N_1$ subtype. The synthetic fusion peptides are preferably selected from the amino acid sequences listed in Table 1 below, wherein the amino acids are identified by their corresponding one letter codes and wherein the sequences are represented by SEQ ID NOS: 1–16 in number order from top to bottom (see also Example 6 and FIG. 2 of WO 92/13525).

Instead of or in addition to influenza virus hemagglutinin, the hemagglutinins from other viruses may also be suitably used as fusion peptides (proteins) for the instant virosomes as long as they exert substantially the same pH-mediated cell penetration mechanism as the influenza hemagglutinin. Candidate hemagglutinins include, for example, rhabdovirus, parainfluenza virus type III, Semliki Forest virus and togavirus, as disclosed in U.S. Ser. No. 07/930,593, now U.S. Pat. No. 6,040,167 (assignee: NIKA HEALTH PRODUCTS LTD.), incorporated herein by reference.

The term "crosslinker" refers to an organic heterobifunctional molecule capable of linking to the surface of vesicles prepared according to this invention and capable of binding polypeptides. In a preferred embodiment of the present invention, this molecule contains a N-hydroxysuccinimide group for coupling to the amino group of phosphatidylethanolamine and a maleimide group for conjugation of monoclonal antibody fragments, such as succinimidyl 4-(N-maleimidomethyl)-cyclohexane-1-carboxylate, m-maleimidobenzoyl-N-hydroxysuccinimide ester, m-maleimidobenzoyl-N-hydroxysulfosuccinimide ester, succinimidyl 4(p-maleimidophenyl)-butyrate, sulfosuccinimidyl 4(p-maleimidophenyl)butyrate; or it contains a N-hydroxysuccinimide group and a photoreactive azido group for coupling to cytokines, such as N-hydroxysuccinimidylsuberate (NHS-SA), N-hydroxysuccinimidyl-4-azidobenzoate (HASAB), N-succinimidyl-6-(4'-azido-2'-nitrophenylamino)hexanoate (SANPAH), N-sulfosuccinimidyl-6-(4'-azido-2-nitrophenylamino)hexanoate.

TABLE 1

| | | |
|---|---|---|
| CCCGLFG | AIAGFIENGWEGMIDG | WYG |
| GLFG | AIAGFIENGWEGMIDG | WYGCCC |
| CCCGLFG | AIAGFIENGWEGMIDG | |
| GLFG | AIAGFIENGWEGMIDG | CCC |
| CCCGLFE | AIAGFIENGWEGMIDG | |
| GLFE | AIAGFIENGWEGMIDG | CCC |
| CCCELFG | AIAGFIENGWEGMIDG | |
| ELFG | AIAGFIENGWEGMIDG | CCC |
| CCCLFG | AIAGFIENGWEGMIDG | |
| LFG | AIAGFIENGWEGMIDG | CCC |
| CCC | PPGAVIGTIALGVATAAGIT | |
| | PPGAVIGTIALGVATAAGIT | CCC |
| CCC | PAGVVIGLAALGVATAAGVT | |
| | PAGVVIGLAALGVATAAGVT | CCC |
| CCC | PIGAIIGGVALGVATAAGIT | |
| | PIGAIIGGVALGVATAAGIT | CCC |

It is preferred that the crosslinker be used in the form of a preformed molecule complex of crosslinker and lipid, notably of crosslinker and phosphatidylethanolamine, or of lipid plus crosslinker plus cell-specific marker.

The term "cell-specific" protein or marker refers to a protein capable of linking to the crosslinker or crosslinker-lipid complex, respectively, and further being capable of binding to the receptor of target cells. In a preferred embodiment of the present invention, this molecule refers to a cell receptor-specific compound such as a monoclonal antibody, an antibody fragment, a cytokine or a growth factor. The cell-specific marker provides for selective detection and binding of target cells and thus improves the action of the fusion peptide concomitantly present in the virosomal membrane. The preferred antibody fragments comprise the $F(ab')_2$ and Fab' fragments, while the cell-specific markers further comprise interleukins and other cytokines, particularly the ones listed in Table 2 below.

TABLE 2

| Cytokines (international abbreviations) | | | |
|---|---|---|---|
| BDNF | IFNα | MIP-1α | PDGF |
| CNTF | IFNβ | MIP-1β | PF-4 |
| EGF | IFNγ | MIP-2 | RANTES |
| Epo | IL-1 to IL-15 | NGF | SCF |
| FGF | LIF | NT-3 | TGFα |
| G-CSF | LT (TNFβ) | NT-4 | TGFβ |
| GM-CSF | MCP-1 to MCP-3 | OSM | TNFα |
| 1-309/TCA-3 | M-CSF | PBP | Tpo |
| γIP-10 | MIF | PBSF | jVEGF |

The term "cationic lipid" as used herein refers to an organic molecule that contains a cationic component and a nonpolar tail, a so-called head-to-tail amphiphile, such as N-[(1,2,3-dioleoyloxy)propyl]-N,N,N-trimethylammonium chloride (DOTMA) (Felgner et al.; Proc Natl Acad USA 84:7413–7417, 1987), N-[1,2,3-dioleoyloxy)-propyl]-N,N,N-trimethylammoniummethylsulfate (DOTAP); or N-t-butyl-N'-tetradecyl-3-tetradecylaminopropionamidine (Ruysschaert et al.; Biochem. Biophys. Res. Commun. 203:1622–1628, 1994). Unless explicitly mentioned otherwise, the term also includes the below defined polycationic lipids.

The term "polycationic lipid" refers to an organic molecule that contains a polycationic component and a nonpolar tail such as the lipospermine: 1,3-dipalmitoyl-2-phosphatidylethanolamido-spermine (DPPES) and dioctadecylamidoglycyl spermine (DOGS) (Behr et al.; Proc. Natl. Acad. USA 86:6982–6986, 1989); 2,3-dioleoyloxy-N-[2 (sperminecarboxamido) ethyl]-N,N-dimethyl-1-propaneaminium trifluoroacetate (DOSPA); 1,3-dioleoyloxy-2-(6 -carboxy-spermyl)-propylamide (DOSPER); N,N,N',N'-tetramethyl-N,N'-bis(2-hydroxyethyl)-2,3-dioleoyloxy-1,4-butanediammonium iodide (THDOB).

The lipids preferably comprise one or more natural or synthetic lipids that are positively charged. By "positively charged" is meant that the lipids have a positive net charge at physiological pH. Thus, "positively charged" lipids, membranes or virosomes shall mean lipids, membranes or virosomes that have a positive net charge at physiological pH. It is not intended to include neutral lipids, e.g., phospholipids of the zwitterionic-type, which have positively charged areas within the molecule but which do not exhibit any net charge at physiological pH due to the presence of negatively charged parts of the molecule which stoichiometrically offset the positive charges.

The terms "nucleic acid" or "genetic material" as used herein comprise short chain DNA or RNA, deoxyribonucleotides, oligodeoxyribonucleotides, oligodeoxyribonucleotide selenoates, oligodeoxyribonucleotide phosphorothioates (OPTs), oligodeoxyribonucleotide phosphoramidates, oligodeoxyribonucleotide methylphosphonates, peptide nucleic acids (PNAs), ribonucleotides, oligoribonucleotides, oligoribonucleotide phosphorothioates, 2'-Ome-oligoribonucleotide phosphates, 2'-Ome-oligoribonucleotide phosphorothioates, ribozymes (RNA molecules with enzymatic activities), genes, plasmids and vectors (cloning vehicles).

The term "virosomes" as used herein refers—in its simplest form—to liposomal vesicles with a bilayer membrane comprising cationic lipids and an internal—preferably aqueous—space, wherein the membrane further contains viral proteins, in particular viral glycoproteins. In the preferred embodiment, the viral proteins comprise at least one fusogenic peptide or protein having full biological fusion activity, particularly the spike glycoprotein hemagglutinin and/or neuraminidase of influenza A (e.g., A/Singapore) virus. It shall be understood that the viral proteins also encompass synthetically produced amino acid sequences corresponding to or equal to the fusion peptide of influenza virus as herein described. The membrane lipids comprise the cationic lipids defined above but may optionally further comprise other natural and/or synthetic lipids, preferably phospholipids such as phosphatidylcholine (PC) and phosphatidylethanolamine (PE).

Although the cationic virosomes of the present invention may in many cases—notably for in vitro cell culture experiments—successfully be applied without cell-specific markers on the membrane, it is particularly preferred for in vivo applications that they further comprise at least one cell-specific marker on the membrane as hereinbefore defined. The mean diameter of the vesicles is in the range of 120–180 nm, as determined by electron microscopy and dynamic light scattering.

The term "full (biological) fusion activity" as used herein shall express that the virosomes of the present invention comprising reconstituted viral proteins in the vesicle membrane have essentially the same fusion activity towards target cells as the intact virus from which they are usually reconstituted. Preferably, the comparison of the cationic virosomes, fusogenicity is drawn to intact influenza A virus. The fusion activity is measured according to known procedures, particularly as reported by Hoekstra et al. (Biochemistry 23:5675–5681,1984), or Luscher et al. (Arch. Virol. 130:317–326, 1993).

Before antisense technology can therapeutically or prophylactically be applied to a patient in need thereof a number of technical problems, particularly relating to the development of a suitable carrier system, need be resolved beforehand. For instance, genetic material such as, e.g., antisense oligonucleotides, can be unstable and break down or be otherwise more or less inactivated before it reaches the target cells and it may thus be necessary to use large quantities of such material entrapped in conventional cationic liposomes. Due to these large amounts a question arises about the potential toxicity in the human or animal body.

By using the cationic virosomes of the present invention as carriers for genetic material these problems can be successfully overcome and undesired side effects due to toxicity can be prevented or at least considerably decreased. This beneficial effect is achieved because the present cationic virosomes have—compared to liposomes or virosomes known hitherto—a far higher activity and efficiency of up to a factor of 1,000–20,000 for the transfer of entrapped genetic material such as antisense oligonucleotides into target cells. As a consequence, it is practically impossible to compare the performance of conventional virosomes or cationic liposomes with the performance of the present cationic virosomes. In order that the invention described herein may be more fully understood, the following examples are set forth. The examples are for illustrative purposes only and are not to be construed as limiting this invention in any respect.

EXAMPLE 1

Preparation of a Cationic Lipid Vesicle With Fully Fusion Active Viral Hemagglutinin Trimers From Influenza Virus Containing Encapsulated Antisense L-myc-FITC (=Fluorescein Labeled)-oligodeoxynucleotides Preparation of DOTAP Virosomes and DOTAP-Phosphatidylcholine (PC)-virosomes Hemagglutinin (HA) from the A/Singapore/6/86 strain of influenza virus was isolated as described by Skehel and Schild (1971), Proc. Natl. Acad. Sci. USA 79:968–972. In short, virus was grown in the allantoic cavity of hen eggs, and was purified twice by ultracentrifugation in a sucrose gradient. Purified virus was stabilized in a buffer containing 7.9 mg/ml NaCl, 4.4 mg/ml trisodiumcitrate-2$H_2O$, 2.1 mg/ml 2-morpholinoethane sulfonic acid, and 1.2 mg/ml N-hydroxyethyl-piperazine-N'-2-ethane sulfonic acid pH 7.3. 53 ml of the virus suspension containing 345 $\mu$g HA per ml were pelletted by ultracentrifugation at 100,000×g for 10 minutes. 7.7 ml of a buffered detergent solution containing 145 mM NaCl, 2.5 mM HEPES and 54 mg/ml of the non-ionic detergent octaethyleneglycol monododecylether (OEG=$C_{12}E_8$), pH 7.4, were added to the influenza virus pellet. The pellet was completely dissolved by using ultrasonication for 2 minutes at room temperature. The solution was subjected to ultracentrifugation at 100,000×g for 1 hour. The obtained supematant contained the solubilized HA trimer (1.635 mg HA/ml) and trace amounts of neuraminidase. 6 mg of DOTAP were added to 3.7 ml of supernatant (6 mg HA) and dissolved. The solution was sterilized by passage through a 0.2 $\mu$m filter and then transferred to a glass container containing 1.15 g of sterile microcarrier beads, preferably Biobeads SM-2. The container was shaken for 1 hour by using a shaker REAX2 from Heidolph (Kelheim, Germany). When necessary, this procedure was repeated up to three times with 0.58 mg of Biobeads. After these procedures a slightly transparent solution of DOTAP virosomes was obtained.

For the production of DOTAP-PC virosomes 3 mg of DOTAP and 3 mg of PC were added to the supernatant containing 6 mg HA, and dissolved. The subsequent steps were the same as described for the DOTAP virosomes.

Preparation of Virosomes With Synthetic Fusion Peptide

One possibility of preparing cationic virosomes carrying synthetic fusion peptides in the membrane comprises the following steps:

1. Activation of phosphatidylethanolamine (PE) by the crosslinker N-[γ-maleimidobutyryloxylsucccinimide ester (GMBS) in a reaction PE+GMBS→MBS-PE+N-Hydroxysuccinimid, as described by Martin et al., Irreversible coupling of immunoglobulin fragments to preformed vesicles; J. Biol. Chem. 257:286–288 (1982).
2. Preparation of lipid vesicles with activated PE (GMB-PE), wherein 20% Phosphatidylcholine, 70% DOTAP and 10% GMB-PE are dissolved in a buffered detergent solution as described above for the HA containing DOTAP virosomes. The subsequent steps of preparing the lipid vesicles are the same as described above for the DOTAP virosomes.
3. Coupling of the synthetic fusion peptide to the lipid vesicles, wherein a peptide comprising 20 amino acids is used having the amino acid sequence G-L-F-E-A-I-A-G-F-I-E-N-G-W-E-G-M-I-D-C, (SEQ ID NO: 17), and which contains a free amino group at the N-terminus and an amide group at the C-terminus. Since the amino acid at the C-terminus is cysteine, there is a free thiol group available for the coupling of the peptide to the GMP-PE in the membrane of the lipid vesicles.

For carrying out the coupling reaction:

$$PE\text{-}GMB_{membrane}+HS\text{-}Cys\text{-}Peptide \rightarrow PE\text{-}GMB_{membrane}\text{-}S\text{-}Cys\text{-}Peptide$$

a solution of freshly prepared lipid vesicles in a buffer (40 mM citric acid, 35 mM disodium phosphate, 100 mM NaCl, and 2 mM EDTA, pH 5.5) is mixed with the peptide solution in the same buffer. The mixture is gently stirred under nitrogen atmosphere overnight at 4° C. Lipid vesicles are separated from unconjugated peptides by gel filtration on a High Load Superdex 200 column.

As an alternative, the fusion peptides may also be coupled to the lipid vesicles my means of preformed PE-crosslinker-peptide complexes as described below in this example for the Fab' fragments.

Incorporation of Phosphorothioate Oligodeoxyribonucleotides Into DOTAP Virosomes The antisense and sense oligodeoxyribonucleotide phosphorothioates (OPTs) of the L-myc gene were used as an example for the demonstration of the high efficiency of cationic virosomes in transfection. 5'-FITC-OPTs were synthesized via phosphoramidite chemistry (Microsynth GmbH, Balgach, Switzerland). The pentadecamer (5'-FITC-GTAGTCCATGTCCGC-3') and the pentadecamer (5'-FITC-GCGGACATGGACTAC-3') were used as the antisense OPT and sense OPT, respectively. A mixed sequence control (msc) OPT consisting of the same length of nucleotides as antisense and sense OPTs was synthesized.

1 ml of DOTAP virosomes or DOTAP-PC virosomes was added to each of a) 2 mg of antisense FITC-OPT (1.3 $\mu$mol)

b) 3.4 mg sense FITC-OPT (1.3 $\mu$mol) and c) 3.1 mg msc FITC-OPT (1.3 $\mu$mol).

The FITC-OPTs were dissolved and the solutions were then treated by sonication for 2 minutes at 26° C. Non-encapsulated FITC-OPTs were separated from the virosomes by gel filtration on a High Load Superdex 200 column (Pharmacia, Sweden). The column was equilibrated with sterile PBS. The void volume fractions containing the DOTAP virosomes with encapsulated FITC-OPT were eluted with PBS and collected. Virosome-entrapped FITC-OPT concentrations were determined fluorometrically after the virosomes were fully dissolved in 0.1 M NaOH containing 0.1% (v/v) Triton X-100. For calibration of the fluorescence scale the fluorescence of empty DOTAP-virosomes that were dissolved in the above detergent solution was set to zero.

Coupling of Fab'-fragments to Virosomes by Means of Preformed Phosphatidylethanolamine-bifunctional Crosslinker Molecule Complexes 3 mg of freshly reduced Fab' from murine monoclonal anti-CD10-(AntiCALLA) antibody, dissolved in 2.8 ml of a citric acid buffer solution (100 mM NaCl, 40 mM citric acid, 35 mM $Na_2HPO_4.2H_2O$, 2 mM EDTA, pH 5.5) were added to a solution of 0.524 mg of N-[4-(p-maleimido-phenyl) butyryl]phosphatidylethanolamine (MPB.PE) in 215 $\mu$l of citric acid buffer containing 0.5% of n-octyl-oligo-oxyethylene. The mixture was then incubated under nitrogen for 16 h at 4° C. with gentle stirring. After incubation the non-coupled MPB.PE was removed by a batch of 400 $\mu$l of freshly reduced wet Thiopropyl Sepharose 6B (Pharmacia, Sweden). The mixture was incubated for 4 h at room temperature. The Thiopropyl Sepharose 6B was removed by centrifugation and the resulting solution neutralized to pH 7.0. The neutralized solution was supplemented with OEG (54 mg/ml).

The solutions prepared as described above were added to the solutions for the preparation of DOTAP virosomes. The Fab'-MPB.PE molecules are inserted into the lipid bilayer during the formation of virosomes.

Electron Microscopy Observations

Micrographs of DOTAP virosomes confirm the preferred unilamellar structure of the vesicles with an average diameter of approximately 120 to 180 nm as determined by laser light scattering. The HA protein spikes of the influenza virus are clearly visible (FIG. 1).

Determination of the Fusion Activity of DOTAP Virosomes

Figure 2:
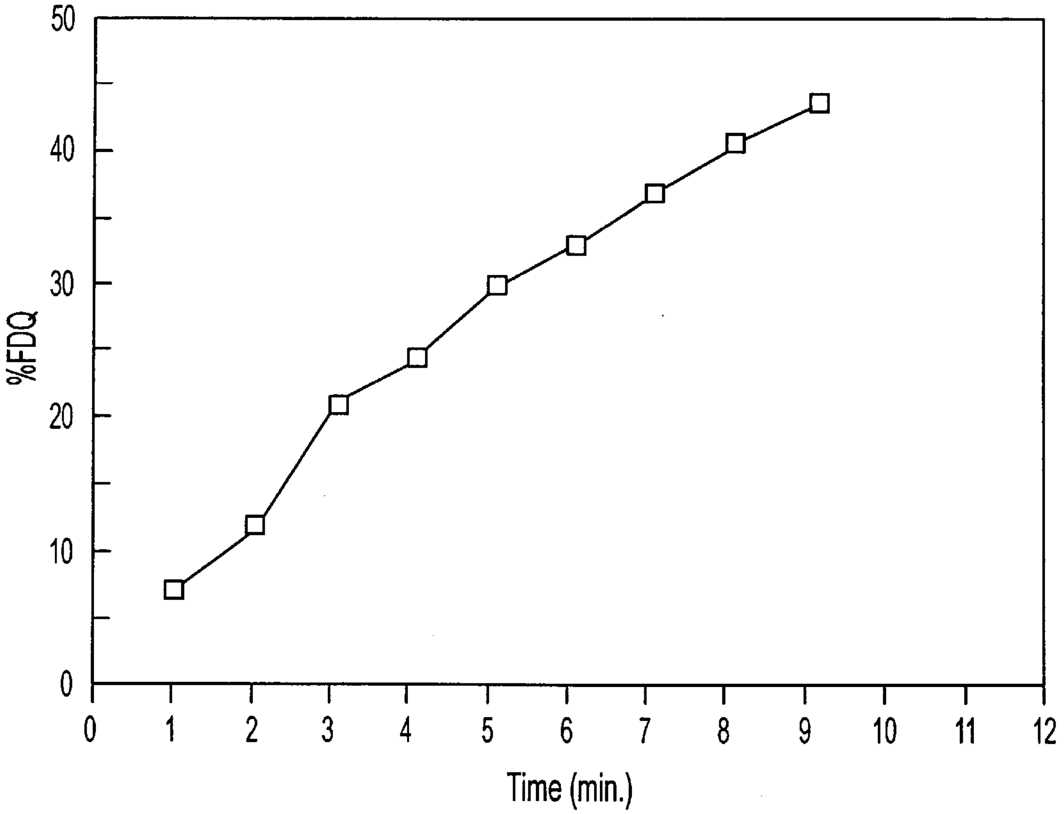
FIG. 2 shows the pH-induced fusion activity of octadecyl rhodamine B labeled DOTAP-virosomes with model liposomes.

The fusion activity of the present DOTAP virosomes was measured by the quantitative assay based on fluorescence dequenching described by Hoekstra et al. (1984), Biochemistry 23:5675–5681 and L. Lüscher et al. (1993), Arch. Virol. 130:317–326. The fluorescent probe octadecyl rhodamine B chloride (R18) (obtained from Molecular Probes Inc., Eugene, USA) was inserted at high densities into the membrane of DOTAP virosomes by adding the buffered OEG ($C_{12}E_8$) solution containing DOTAP and HA to a thin dry film of the fluorescent probe, followed by shaking for 5 to 10 minutes for dissolving the probe, then continuing as described above under "Preparation of a cationic lipid vesicle . . . ". Dilution of the quenching rhodamine was observed by incubation of the rhodamine-labeled DOTAP virosomes with model liposomes (ratio of DOTAP:liposomal phospholipid=1:20). The fluorescence was measured by a Perkin-Elmer 1000 spectrofluorimeter at 560 and 590 nm excitation and emission wavelengths, respectively. FIG. 2 shows the pH-induced fusion reaction of DOTAP virosomes expressed as percent of fluorescence dequenching (% FDQ).

Cellular Uptake of Encapsulated Antisense-L-myc-FITC-OPT

Figure 3:
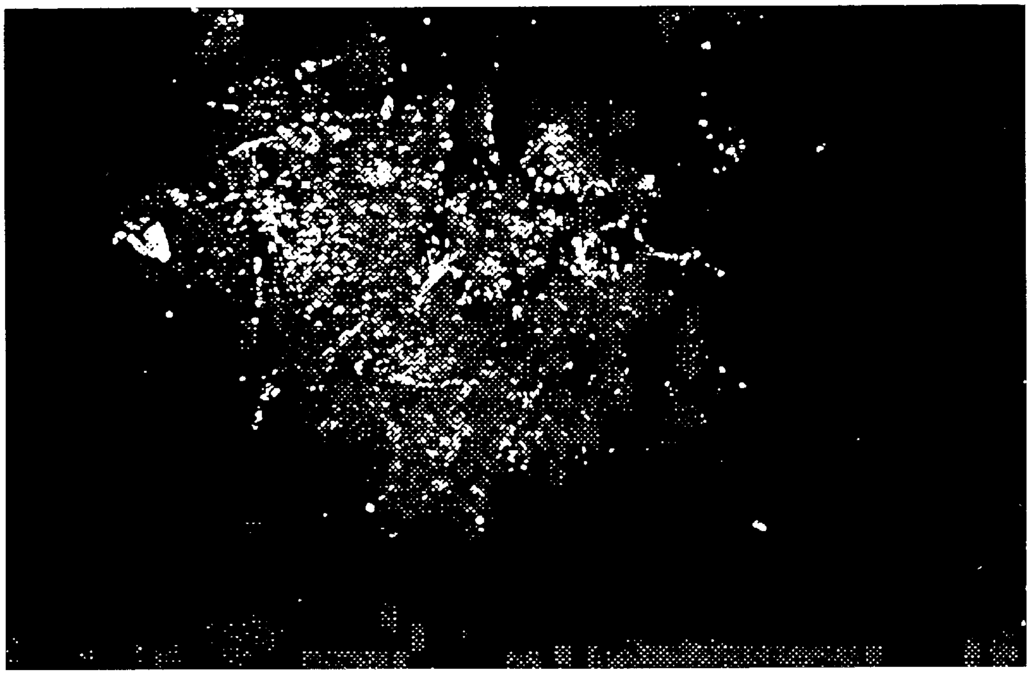
FIG. 3 shows DOTAP-virosomes with encapsulated antisense FITC-OPT incorporated into human small cell lung cancer cells.

It proved very useful to label the OPT with fluorescein to study the mechanism of cellular uptake of DOTAP virosomes. Human small cell lung cancer cells (ATCC-NCI-H209) which express high levels of L-myc gene (Nau et al. 1985; Nature 318, 69–73) were grown in 2-well tissue culture chamber slides (Nunc, Naperville, Ill. 60566, USA). 50 $\mu$l of FITC-OPT-virosomes were added to the cells. They were incubated for 5, 15, and 30 min at 37° C., washed twice with PBS and then examined by fluorescence microscopy. DOTAP virosomes with encapsulated antisense FITC-OPT were rapidly incorporated into the cells as can be seen in FIG. 3.

Examination of the Biological Effect of Antisense-L-myc-FITC-OPT-DOTAP Virosomes Measured by the Thymidine Incorporation Method Human small cell lung cancer cells (ATCC-NCI-H209 American Type Culture Collection, Rockville, USA) were cultured in 24-well Costar plates at an initial concentration of $1 \times 10^5$ per well and per ml. After an incubation of 24 hours, medium was removed and 625 $\mu$l of fresh medium containing 0.5 $\mu$Ci $^{14}$C-thymidine (prepared from (2-$^{14}$CI thymidine, 52.0 mCi/mmol; Amersham, England) and 75 $\mu$l of DOTAP virosomes containing 0.2 nmol of either antisense, sense, or msc FITC-OPTs were added. The cultures were gently shaken at very slow agitation for 1 hr at 37° C. and then transferred to the incubator. After 48 hours the cell suspensions were removed, transferred to centrifuge vials, and centrifuged. Obtained cell pellets were washed twice. When the cells could not sufficiently be dispersed into a single cell suspension, they were exposed briefly to a trypsin/EDTA solution. Cell pellets were dissolved in 1.5 ml of 0.1 M NaOH/Triton-X-100 (0.1%) solution. 3 ml of liquid scintillation cocktail (Ready Protein+, Beckman, Fullerton, Calif., USA) were added to 1 ml of solution. $^{14}$C-radioactivity was counted in a liquid scintillation counter (Beckman, Fullerton, Calif., USA).

Figure 4:
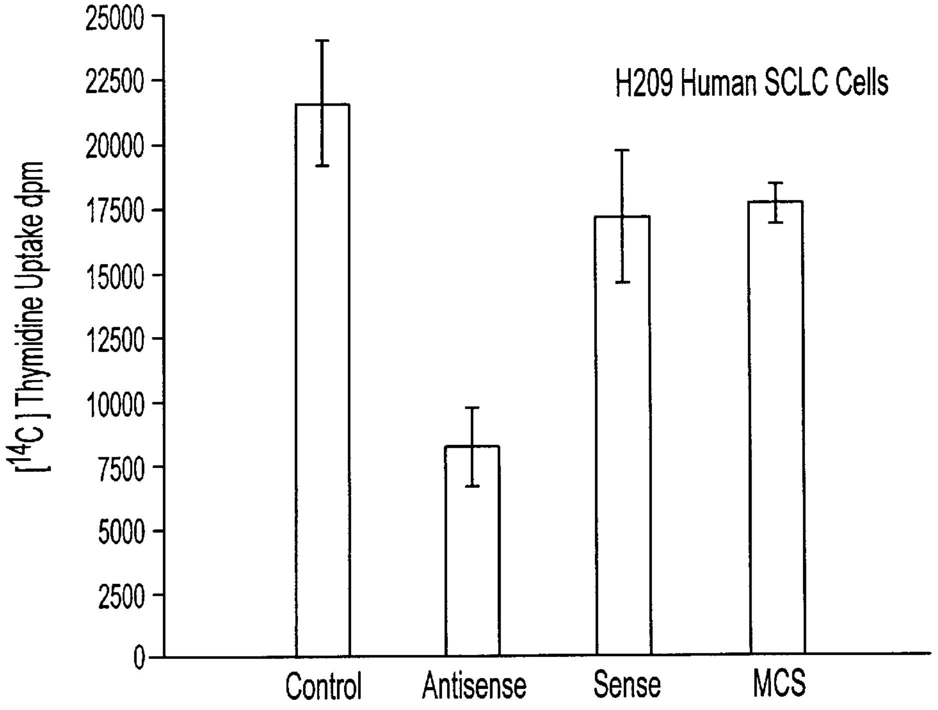
FIG. 4 and FIG. 5 show the extraordinary uptake and transfection efficiency of antisense-L-myc-DOTAP-virosomes into human small cell lung cancer cells.
Figure 5:
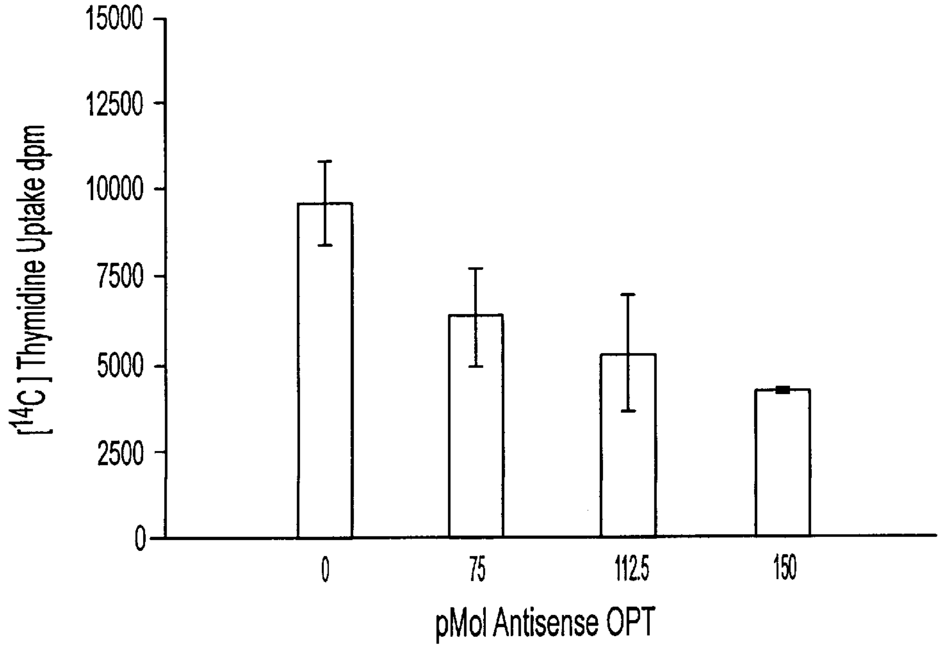

FIGS. 4 and 5 clearly demonstrate the extraordinary uptake and transfection efficiency of antisense-L-myc-DOTAP virosomes.

Figure 6:
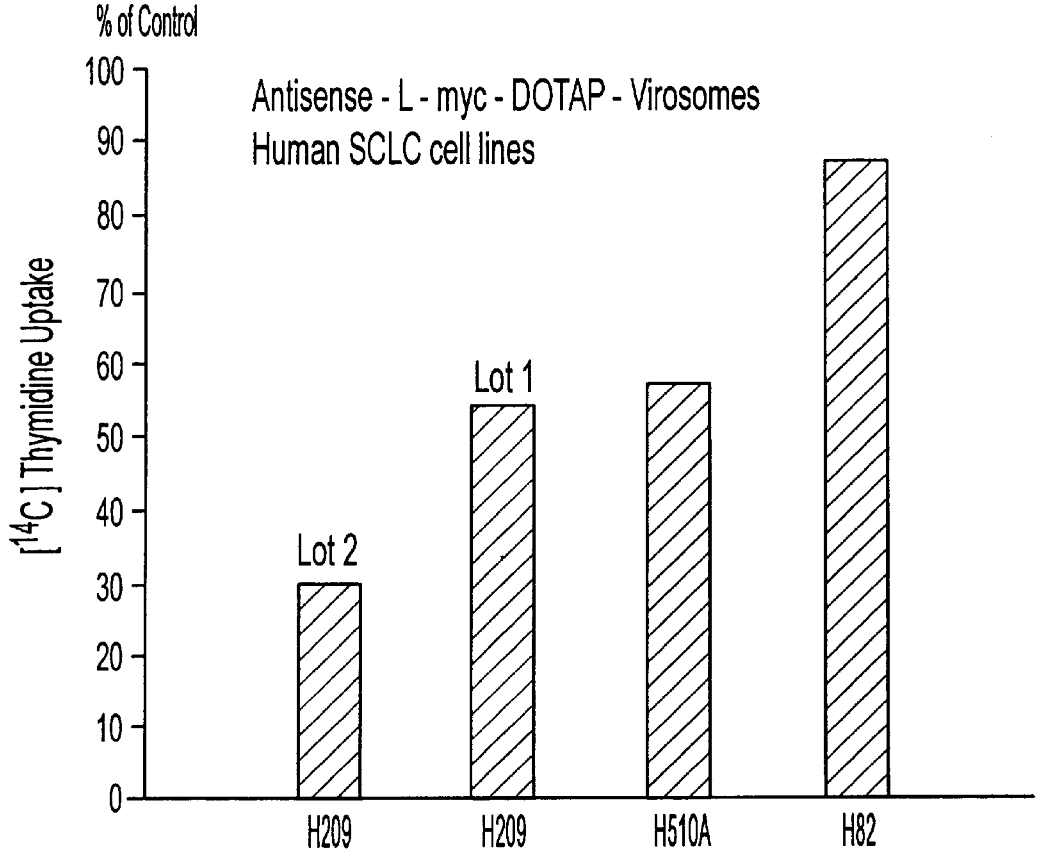
FIG. 6 shows the incubation of different human small cell lung cancer cells, with Antisense-L-myc virosomes.

FIG. 6 demonstrates that calls that do not express L-myc are not influenced or inhibited by the antisense-L-myc virosomes. Also, empty virosomes did not show any effects on cancer cells and normal cells. It appears therefore that an anti-cancer therapy with antisense OPT encapsulated in the present virosomes may have a great potential, particularly because of their lack of the hereinbefore mentioned disadvantages of conventional cationic liposomes.

EXAMPLE 2

Preparation of a Cationic Lipid Vesicle With Fully Fusion Active Viral Hemagglutinin Trimers From Influenza Virus Containing the Encapsulated Vector pcDNA3 with Human IL-6 Gene Cloned Into the Polylinker Site (=pcDNA3-IL-6)

Preparation of DOTAP Virosomes and Incorporation of pcDNA3-IL-6 pcDNA3 (Invitrogen Corporation, San Diego, USA) is a 5.4 kb vector designed for high-level stable and transient expression in eukaryotic hosts. HA was isolated and purified as described in Example 1.

4 mg of DOTAP were dissolved in 0.5 ml of the buffered detergent solution containing 145 mM NaCl, 2.5 mM HEPES and 54 mg/ml of OEG (=$C_{12}E_8$), pH 7.4, and added to 2 ml of supernatant containing 4 mg HA. To the resulting mixture 100 μg of pcDNA3-IL-6 were added and dissolved. The solution was subjected to ultrasonication for 30 seconds. OEG was removed by Biobeads as described in Example 1.

Transfection of DOTAP Virosomes Loaded With pcDNA-IL-6 Into Murine Myeloma Cells The obtained solution comprising the pcDNA-IL-6 loaded DOTAP virosomes was diluted 1:1000 with PBS. 20 μl and 50 μl of this solution containing 1 ng and 2.5 ng pcDNA-IL-6, respectively, were added to $2\times10^6$ myeloma cells (P3/NSI/1-Ag4-1; American Type Culture Collection, Rockville, USA). After 48 h incubation the supernatants of the cell cultures were tested for human IL-6 by an ELISA assay. A content of 20 to 45 pg IL-6 per ml was measured.

Comparison of Transfection Efficiency of pcDNA-IL-6 Loaded DOTAP Virsomes With pcDNA-IL-6 Loaded DOTAP Liposomes No IL-6 was found in myeloma cell cultures transfected with conventional DOTAP liposomes (which are devoid of viral fusion peptides) containing the same amount of pcDNA-IL-6 as the DOTAP virosomes. In order to obtain the same transfection results as with the pcDNA-IL-6 loaded DOTAP virosomes it was necessary to increase the amount of the pcDNA-IL-6 loaded DOTAP liposomes by a factor of one thousand 1000.

EXAMPLE 3

Preparation of a Cationic Lipid Vesicle With Fully Fusion Active Viral Hemagglutinin Trimers From Influenza Virus Containing the Encapsulated Vector pRSVcat Preparation of DOTAP Virosomes and Incorporation of pRSVcat The expression vector pRSVcat (from ATCC, Rockville, USA) contains the CAT gene which codes for the chloramphenicol acetyltransferase (CAT). The enzyme catalyzes the transfer of an acetyl group from acetyl-CoA to the 3'-hydroxy position of chloramphenicol. CAT vectors are useful for monitoring transfection efficiency in general. pRSVcat was encapsulated into DOTAP virosomes under the conditions described in Example 2.

Transfection of DOTAP Virosomes Loaded With pRSVcat Into Jurkat Cells

Jurkat cells ($10^6$ cells/ml) were incubated with different amounts of pRSVcat-loaded DOTAP virosomes (0.0001 μl–25 μl). After 48 hours incubation at 37° C. the CAT activity in the Jurkat cells was measured by the CAT-ELISA assay (Boehringer Mannheim, Germany).

Figure 7A:
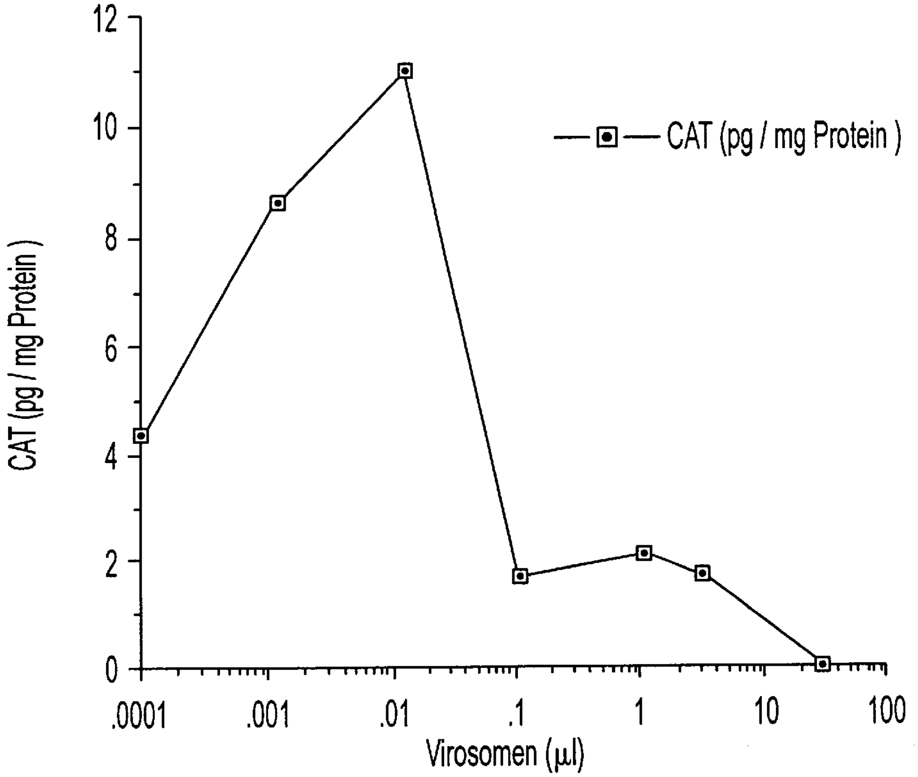
FIG. 7*a*, 7*b* show the transfection efficiency of pRSVcat-DOTAP virosomes for Jurkat cells.
Figure 7B:
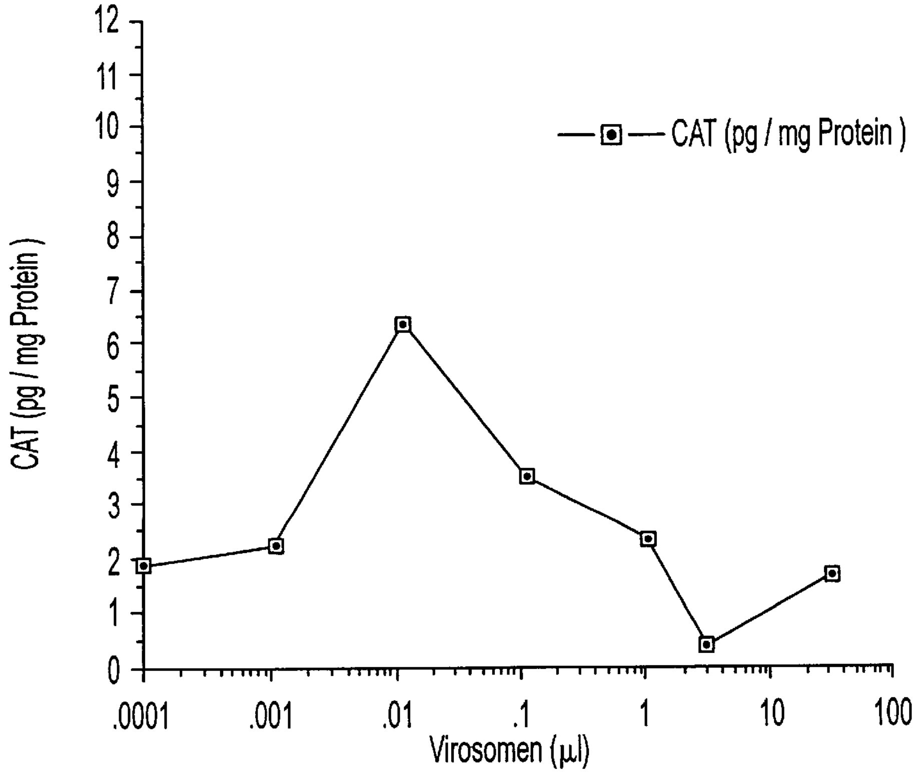

FIGS. 7*a* and 7*b* demonstrate that a maximum transfection is achieved by addition of 0.01 μl of DOTAP virosomes. Contrary to the aforementioned, the addition of 0.01 μl of pRSVcat-loaded DOTAP liposomes to Jurkat cells under the same incubation conditions did not result in any detectable CAT activity.

EXAMPLE 4

Uptake of Virosomes By Cells

Entry of virosomes into target cells can be divided into two distinct steps:

1. Attachment
2. Penetration.

Attachment involves binding of the virosomes via HA to the cell receptors which are membrane glycoproteins or glycolipids with a terminal sialic acid. In case of specific virosomes Fab' fragments will additionally recognize antigenic structures on the target cell surface, resulting in an attachment to target cells by two different binding mechanisms. Thus, specific virosomes exert a selectivity for special cell types. Virosomes with Fab' fragments that recognize tumor associated antigens such as TAG72, CEA, 17-1A, CA19-9 or leukemia associated antigens such as CD10 (CALLA) and CD20 will bind selectively to tumor or leukemia cells carrying the mentioned antigens on their cell surface. The hemagglutinin glycoproteins are carefully isolated and purified. There is no inactivation either by proteolytic digestion or by reduction of its intramolecular disulfide (—S—S—) bonds.

Figure 8:
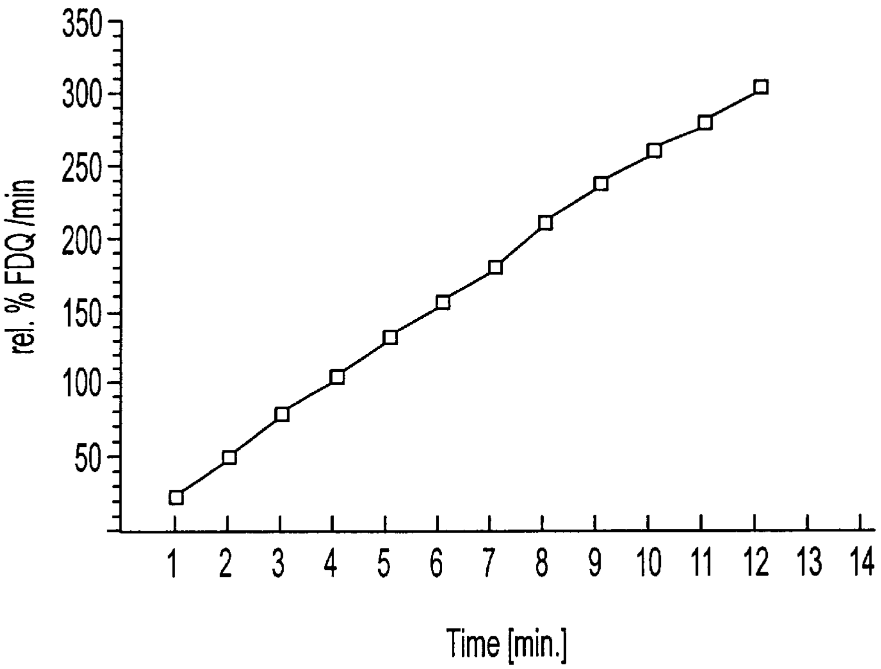
FIG. 8: Fusion of DOTAP-virosomes with phospholipid-liposomes. Fusion was measured with the R18 assay at 37° C.

Penetration involves entry of virosomes into the cells by receptor-mediated endocytosis. The virosomes get trapped in endosomes. The acidic pH (5–6) within the endosomes triggers fusion of the virosomal membrane with the endosomal membrane. The fusion is mediated by the viral spike glycoprotein hemagglutinin (HA). The membrane fusion reaction in the endosome liberates the virosome from its lipid envelope and provides access for the encapsulated drugs to the cytosol. Fusion activity of these virosome-preparations were tested by fluorescence dequenching. Virosomes were labeled with the fluorescent probe octadecyl rhodamine B (R18) and the fusion activity of HA was monitored as fluorescence dequenching due to the dilution of the probe from the virosomal into a liposomal target membrane. FIG. 8 shows the fluorescence observed upon addition of DOTAP-virosomes, labeled with R18, to phospholipid-liposomes. The fluorescence started to increase rapidly indicating an intact HA mediated fusion.

Time Dependent Uptake by Cells

The uptake of virosomes was measured by incubation of cells with $^{14}C$-labeled virosomes. P3/NS1 cells at a concentration of $1\times10^5$/ml were incubated with 40 μl of virosomes at 37° C. for 5, 10, 15, 20 and 30 minutes. After washing, the cells were lysed and the amount of $^{14}C$-label virosomes was measured. As can be seen in Table 3, the cellular uptake is very fast: During the first five minutes 10% of the virosomes were incorporated. Longer incubation times did not enhance the uptake any further. 1 ml of virosome solution contained approximately $10^{11}$–$10^{12}$ virosomes, hence 4,000–40,000 virosomes per cell were incorporated within 5 minutes.

TABLE 3

| Incubation Time (min) | dpm |
|---|---|
| 5 | 6414 |
| 10 | 6832 |
| 15 | 6096 |
| 20 | 6610 |
| 30 | 6626 |

EXAMPLE 5

Antisense Strategies in the Treatment of Cancers

So-called "antisense" oligodeoxynucleotides (ODN) are short nucleotide sequences of DNA synthesized as reverse complements of the desired mRNA target's nucleotide sequence. By formation of the RNA-DNA duplex translation of the message is prevented and the destruction of the molecule by RNase H is promoted. Delivery of ODN targeting oncogene-encoded mRNA to cancer cells may be associated with inhibition of cell proliferation and, in some circumstances, cell death.

Antisense ODN have a great potential as therapeutic agents. Many preclinical animal studies as well as clinical trials of Phases I–III have shown that antisense ODN directed against oncogenes and viral genes are therapeutically active.

Transfer of functional DNA molecules into cells by DNA-loaded liposomes or conventional virosomes is not very efficient. Therefore virosomes with a positively charged lipid bilayer (cationic) were developed for transfer of genetic material. The positively charged lipid bilayer interacts with nucleic acids and causes them to concentrate within the vesicles formed.

Antisense-L-myc-virosomes

Figure 9:
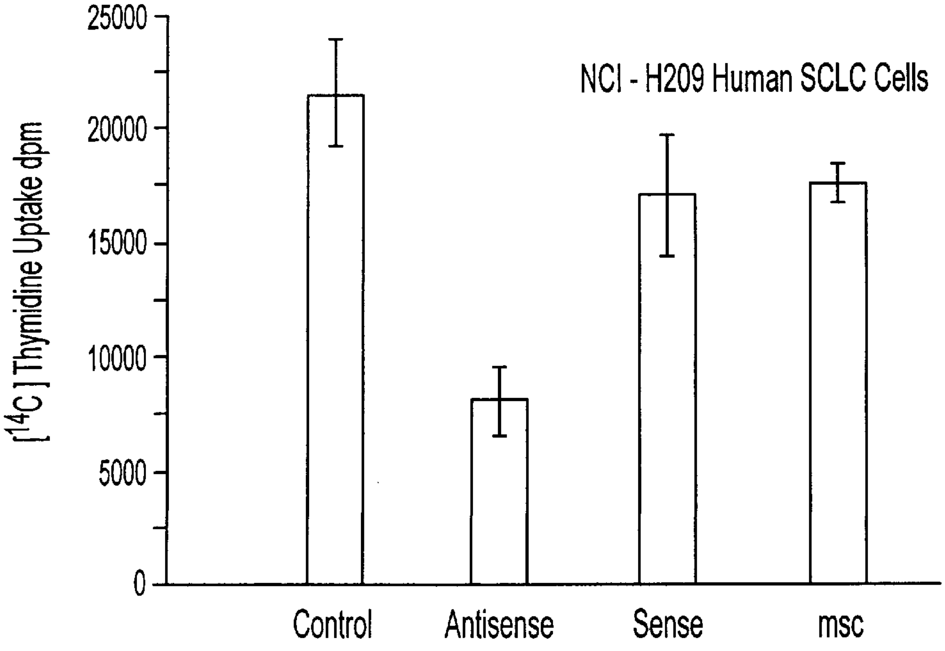
FIG. 9: Thymidine incorporation into virosome-treated NCI-H209 cells. 75 $\mu$l of virosomes containing 200 picomol of either antisense, sense, or msc FITC-OPT and 625 $\mu$l of fresh medium containing 0.5 $\mu$Ci $^{14}$C-thymidine were added to $5\times10^4$ cells/ml per well.

The L-myc gene, first discovered in a small cell lung cancer (SCLC) cell line, is frequently amplified and overexpressed in SCLC. 5'-FITC-phosphorothioate oligodeoxyribonucleotides (OPT) were synthesized via phosphoramidite chemistry (Microsynth GmbH, Balgach, Switzerland). The pentadecamer (5'-FITC-GTAGTCCATGTCCGC-3') and the pentadecamer (5'-FITC-GCGGACATGGACTAC-3') were used as the antisense OPT and sense OPT, respectively. A mixed sequence control (msc) OPT consisting of the same length of nucleotides as antisense and sense OPT was synthesized. The antisense OPT covering the translational initiation site acts by inhibiting ribosomal translation of the target mRNA. Antisense-L-myc-phosphorothioate oligodeoxyribonucleotides were encapsulated into the virosomes. The antiproliferative effect of virosome-encapsulated L-myc antisense DNA in the SCLC cell lines H209, H510, and H82 was evaluated. Antisense-L-myc virosomes were added to the cells of human small cell lung cancer cell lines. Sense-L-myc virosomes and msc (mixed sequence control)-virosomes were used as controls (FIG. 9).

Figure 10:
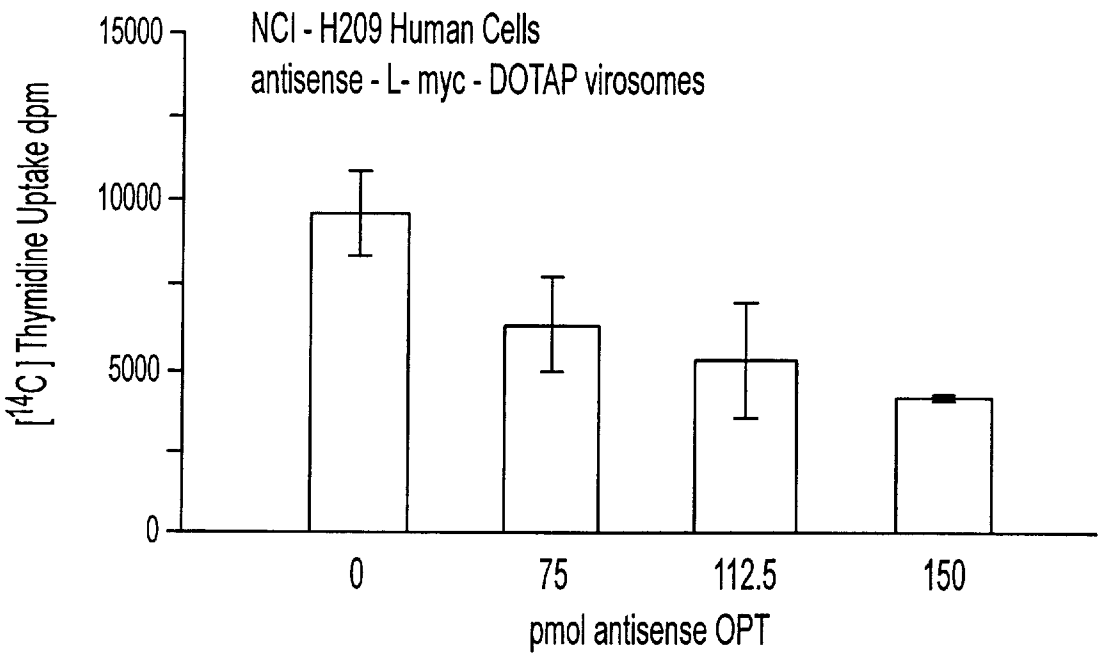
FIG. 10: Dose-dependent inhibition of thymidine incorporation into NCI-H209 cells upon addition of virosomes containing antisense-L-myc-OPT. NCI-H209 cells were incubated at an initial cell concentration of $1\times10^5$ per well and per ml. Values are the means±standard deviations of three experiments

Antisense-L-myc virosomes were 20,000-fold more active than non-encapsulated antisense OPT. To induce the same effects as seen in FIG. 10 concentrations of non-encapsulated L-myc-antisense OPT in the range of micromoles had to be added to the cell cultures. Hence, cationic virosomes are far more efficient in the delivery of ODN than the cellular uptake of nonencapsulated ODN and also more efficient than cationic liposomes.

Figure 11:
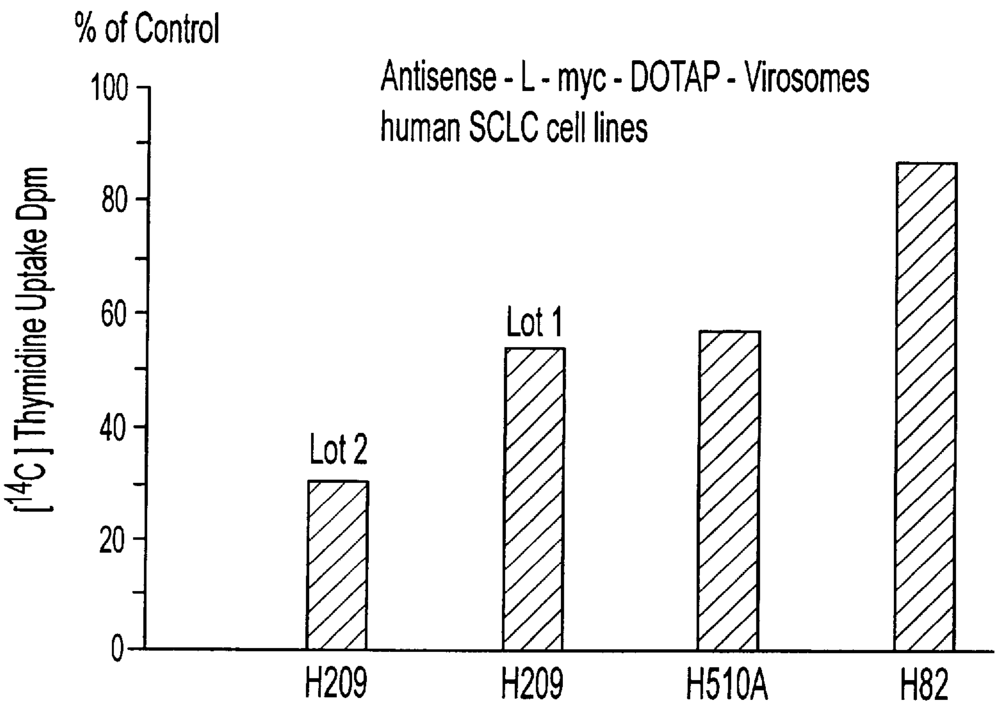
FIG. 11: Incubation of different human small cell lung cancer cell lines with 75 $\mu$1 of antisense-L-myc virosomes. L-myc oncogen expression decreases in the cell lines as indicated: H82<H51OA<H209. The virosomes of lot 1 contained a smaller amount of antisense-L-myc than the ones of lot 2.

The growth-inhibitory effect of antisense-L-myc virosomes correlated with levels of L-myc expression in the three SCLC cell lines, H209, H510, and H82. From FIG. 11 it was concluded that those cells that do not express the L-myc gene are not influenced by antisense-L-myc virosomes. Empty cationic virosomes did not show any or only minor effects on normal cells and cancer cells. Since the L-myc gene is frequently amplified and overexpressed in SCLC and very restricted and low-level expressed in human adult tissues, L-myc might be a good target for an antisense virosome therapy.

EXAMPLE 6

Non-Infectious Transfer of Plasmid-based Vectors For Gene Therapy: Transfection of Vectors for Mammalian Expression by Cationic Virosomes Current approaches to cancer gene therapy use plasmid-based vectors to express suitable target genes in human cancer cells either ex vivo or in vivo. The following therapeutic gene targets are evaluated: Susceptibility genes such as herpes simplex virus thymidine kinase (HSV-TK) genes (Moolten F L; Cancer Res. 46:5276–5281,1986); genes which target the immune system to eliminate cancer cells such as cytokine genes (Tepper R I et al.; Cell 57:503–512, 1989), genes coding for costimulatory molecules (Townsend S E et al.; Science 259:368–370, 1993), foreign histocompatibility genes (Plautz G E et al.; Proc Natl Acad Sci USA 90: 4645–4649, 1993); and replacement of wild-type tumor suppressor genes such as p53 (Chen P L et al.; Science 250:1576–1580, 1990).

Because of certain limitations of currently used viral-based vectors for gene therapy such as, for instance, lack of specificity in targeting tumor cells for gene transfer, and because of safety concerns regarding the possible induction of secondary malignancies and the possibility of recombination to form replication competent virus, a non-infectious gene transfer technology for in vivo gene delivery of plasmid-based expression vectors needed to be developed. The use of the herein disclosed cationic virosomes is a promising alternative of a non-infectious, receptor-mediated gene transfer technology.

The typical transfection efficiencies by using commercially available lipids are between 5–50%. Not only provide virosomes higher transfection efficiency than commercially available liposomes but the entrapment of DNA into virosomes results also in stable transformation of cells.

Human interleukin 6 (IL-6) gene was cloned into the polylinker site of pcDNA3, a 5.4 kb vector designed for high-level stable and transient expression in eukaryotic hosts. The vector contains the neomycin resistance marker, expressed from the SV40 early promoter for the selection of stable transformants in the presence of G418.

Encapsulation of the vector was performed by 3 different methods:

1. Dialysis: Plasmids were encapsulated during formation of virosomes. Detergent Octyl-POE (from Alexis Corp., Laeufelfingen, Switzerland) was removed by dialysis.
2. Biobeads: Plasmids were encapsulated during formation of virosomes. Detergent OEG was removed by Biobeads.
3. Ultrasonication: Plasmids were encapsulated by DOTAP and the obtained DOTAP-liposomes were fused with DOTAP-virosomes by ultrasonication.

$^{14}C$-thymidine-labeled pcDNA3-clL-6-DNA was produced for measuring the amount of encapsulated plasmid.

| Method of encapsulation | Amount of encapsulated plasmid |
|---|---|
| Dialysis (1) | 0.02 $\mu$g DNA per $\mu$l of virosomes |
| Biobeads (2) | 0.009 $\mu$g DNA per $\mu$l of virosomes |
| Ultrasonication (3) | 0.04 $\mu$g DNA per $\mu$l of virosomes |

Figure 12:
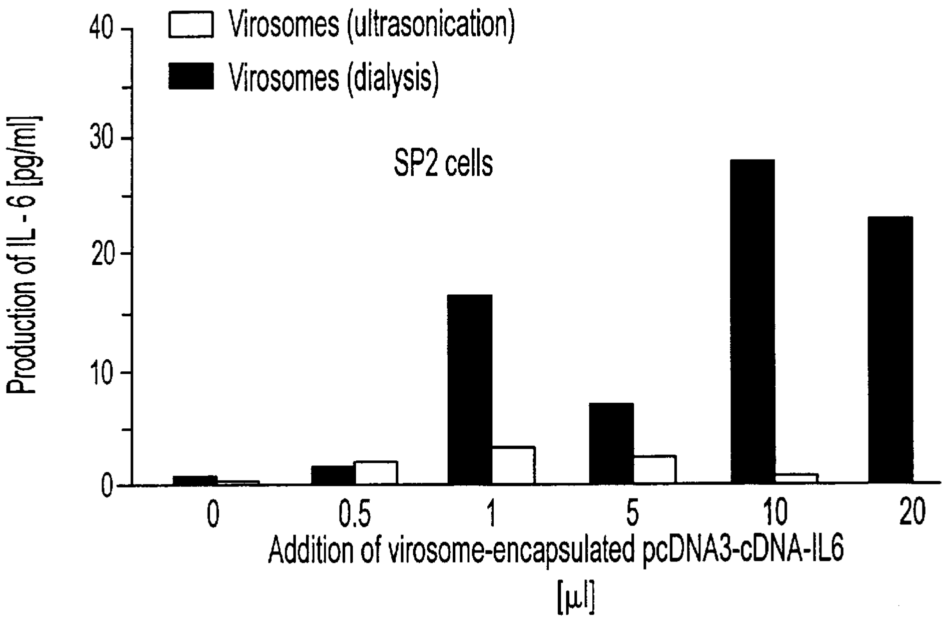
FIG. 12: Transfection of Sp2 cells by two differently produced virosome preparations.
Figure 13:
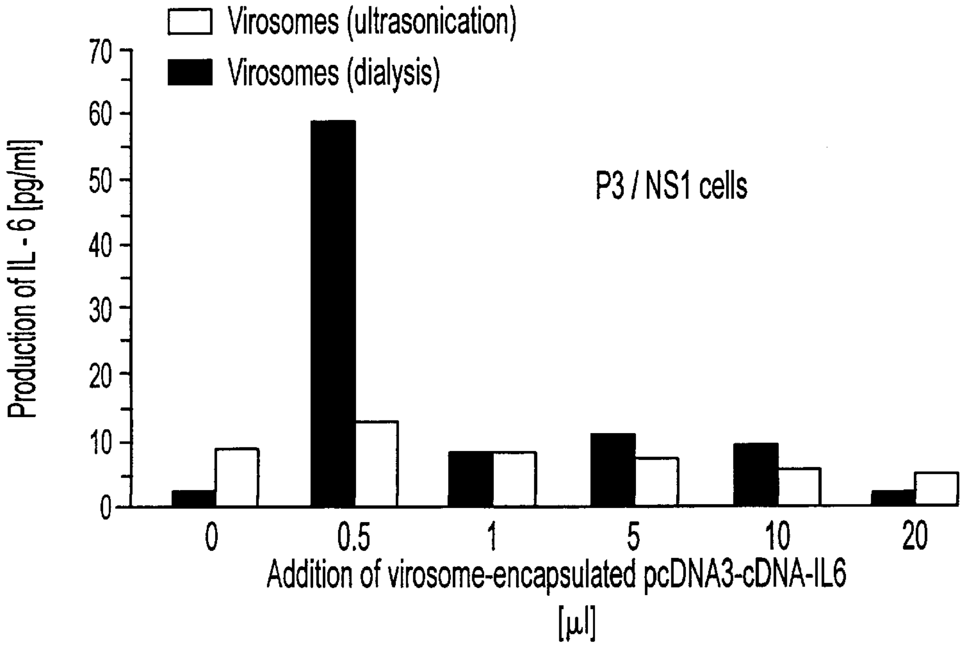
FIG. 13: Transfection of P3/NS1 cells by two differently produced virosome preparations.
Figure 14:
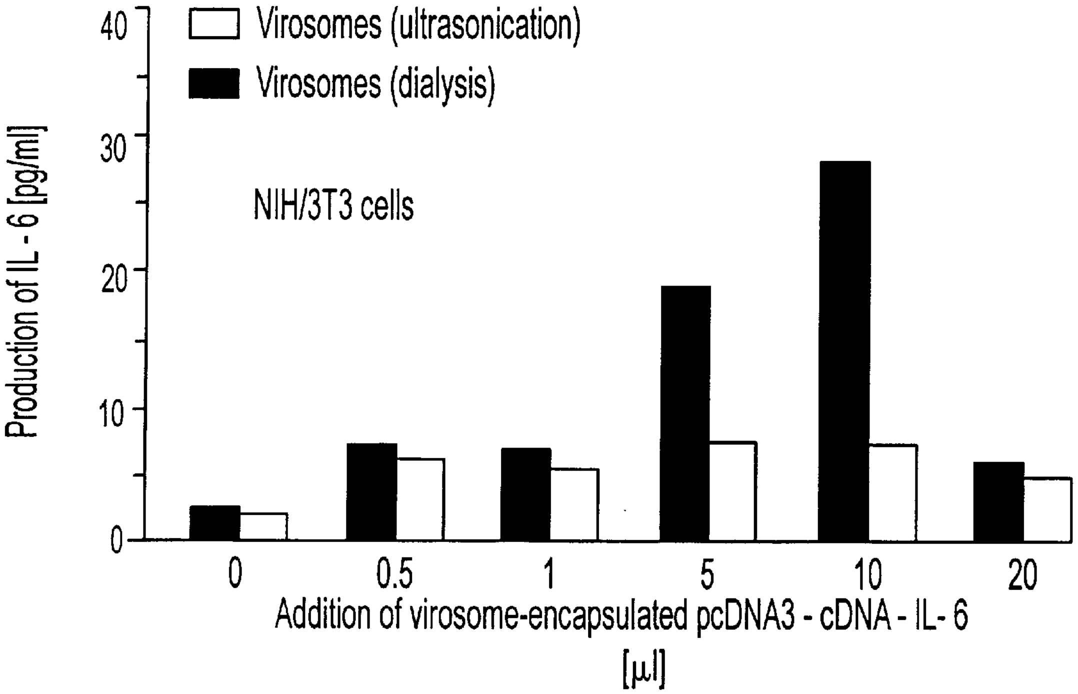
FIG. 14: Transfection of NIH/3T3 cells by two differently produced virosome preparations.

Sp2/0-Ag14 cells (Hybrid, non-secreting, mouse; ID-No: ATCC CRL-1581; herein termed Sp2), P3/NSI/1-Ag4-1 cells (Non-secreting myeloma, mouse; ID-No: ATCC TIB-18; herein termed P3/NS1) and NIH/3T3 cells (Embryo, contract-inhibited, NIH Swiss mouse; ID-No: ATCC CRL-1658) at a cell concentration of $1\times10^5$ in 1 ml medium were transfected by the virosome preparations (1)–(3). Ten days after transfection the amounts of expressed IL-6 were measured by ELISA (FIG. 12, FIG. 13, FIG. 14). All cell lines are available from ATCC, 12301 Parklawn Drive, Rockville, Md., USA.

Transfected Sp2 and P3/NS1 cells were selected twice by G418. After 2 months of culturing the production of IL-6 was measured again. The values are listed in Table 4.

Table 4: Production of IL-6 by transfected cells after re-selection with G418 mia (CML) cases in blast crisis (Calabretta B et al.; Proc Natl Acd Sci USA 88:2351–2355, 1991).

TABLE 4

Production of IL-6 by transfected cells after re-selection with G418

| Cell line | | Method of preparation | Number of cells per ml | Total number of cells | IL-6 [pg/ml] | Total amount of IL-6 [pg] | IL-6 [pg/$10^6$ cells] |
|---|---|---|---|---|---|---|---|
| P3/NS1 | Pellets of cells | Dialysis | $1.2 \times 10^6$ | $6.0 \times 10^6$ 3 ml buffer | 277 | 831 | 138 |
| | | Biobeads | $1.6 \times 10^6$ | $7.8 \times 10^6$ 4 ml buffer | 32 | 128 | 16 |
| | | Ultrasonication | $1.54 \times 10^6$ | $8.0 \times 10^6$ 4 ml buffer | 289 | 1156 | 144 |
| P3/NS1 | Supernatant | Dialysis | | 5 ml supern. | 8 | 40 | 6.7 |
| | | Biobeads | | 4.9 ml supern | 4 | 20 | 2.5 |
| | | Ultrasonication | | 5.2 ml supern. | 25 | 130 | 16.2 |
| Sp2 | Pellets | Dialysis | $2.25 \times 10^6$ | $1.13 \times 10^7$ 5.5 ml buffer | >1200 | >6600 | >584 |
| | | Biobeads | $1.8 \times 10^6$ | $9.5 \times 10^6$ in 4.5 ml buffer | 232 | 1044 | 110 |
| | | Ultrasonication | $2.8 \times 10^6$ | $1.37 \times 10^7$ 7 ml buffer | 680 | 4760 | 347 |
| Sp2 | Supernatant | Dialysis | | 5 ml supern. | 268 | 1340 | 119 |
| | | Biobeads | | 5.2 ml supern. | 8 | 42 | 4.4 |
| | | Ultrasonication | | 4.9 ml supern. | 651 | 3190 | 233 |

The volume of lysis buffer added to the cell pellets was adjusted so that a cell number of ca. $2\times10^6$ per ml was obtained.

EXAMPLE 7

Antisense Strategies in the Treatment of Leukemias

The most common genetic abnormality in human leukemias is the Philadelphia Chromosome ($Ph^1$) translocation. The translocation of the protooncogene abl from chromosome 9 to the breakpoint cluster region (bcr) on chromosome 22 results in the formation of bcr-abl hybrid genes. The abl protooncogene normally encodes a protein with tyrosine kinase activity which is augmented in cells carrying bcr-abl hybrid genes. The bcr-abl transcripts are found in the vast majority of chronic myelogenous leukemia (CML) patients and in $Ph^1$ acute lymphocytic leukemia patients. The targeting of bcr-abl genes in CML is clearly the most rational therapeutic procedure. Synthetic ODN complementary to the junction of bcr-abl transcripts produced from the splicing of either the second or third exon of the bcr gene to the second exon of c-abl were shown to suppress Philadelphia 1 leukemic cell proliferation in vitro and to spare the growth of normal marrow progenitors (Szczylik C et al.; Science 253:562–565, 1991). However, the bcr-abl antisense therapy is restricted to CML patients.

Another molecular target for antisense therapy is the myb gene. Myb, the encoded product of the protooncogene c-myb, functions as a DNA binding specific transcription factor. It is preferentially expressed in hematopoietic cells and is required for hematopoietic cell proliferation. A 18-mer antisense ODN targeted to codons 2–7 of c-myb strongly inhibited or completely abolished clonogenic growth of a T-cell leukemia line (CCRF-CEM), as well as 78% of primary acute myelogenous leukemia cases examined, and 4 of 5 primary chronic myelogenous leukemia (CML) cases in blast crisis (Calabretta B et al.; Proc Natl Acd Sci USA 88:2351–2355, 1991).

Purging of bone marrow is used as a component in the treatment of several neoplasms, including acute and chronic leukemias. At present, marrow is cleansed of leukemic cells by a variety of agents such as immunologic reagents and chemotherapeutic drugs. Virosome encapsulated ODN targeted against one oncogene that confers a growth advantage to leukemic cells will prove therapeutically useful and, most important, more selective than conventional chemotherapeutic agents in eliminating leukemic cells while sparing normal progenitor cells.

Antisense-c-myb Virosomes

Sense and antisense OPT corresponding to c-myb codons 2–9 were prepared. The sense and antisense c-myb sequences were 5'-GCCCGAAGACCCCGGCAC-3' (SEQ ID NO: 18) and 5'-TGTGCCGGGGTCTTCGGGC-3' (SEQ ID NO:19), respectively. Encapsulation of OPT into DOTAP-virosomes was performed by the same method used for L-myc DOTAP virosomes. The human myeloid leukemia cell line KG-1 and the human acute lymphoblastic leukemia cell line CEM-C3 were exposed to sense and antisense c-myb virosomes. Proliferation of KG-1 cells is dependent on the protooncogene myb gene product, whereas CEM-C3 cells are not dependent on the product of c-myb gene. KG-1 cells were incubated with 25, 50, and 100 $\mu$l of sense and antisense c-myb virosomes containing 18, 36, and 72 pmol of sense and antisense OPT, respectively. The number of cells was determined at days 2, 3 and 4.

Figure 15:
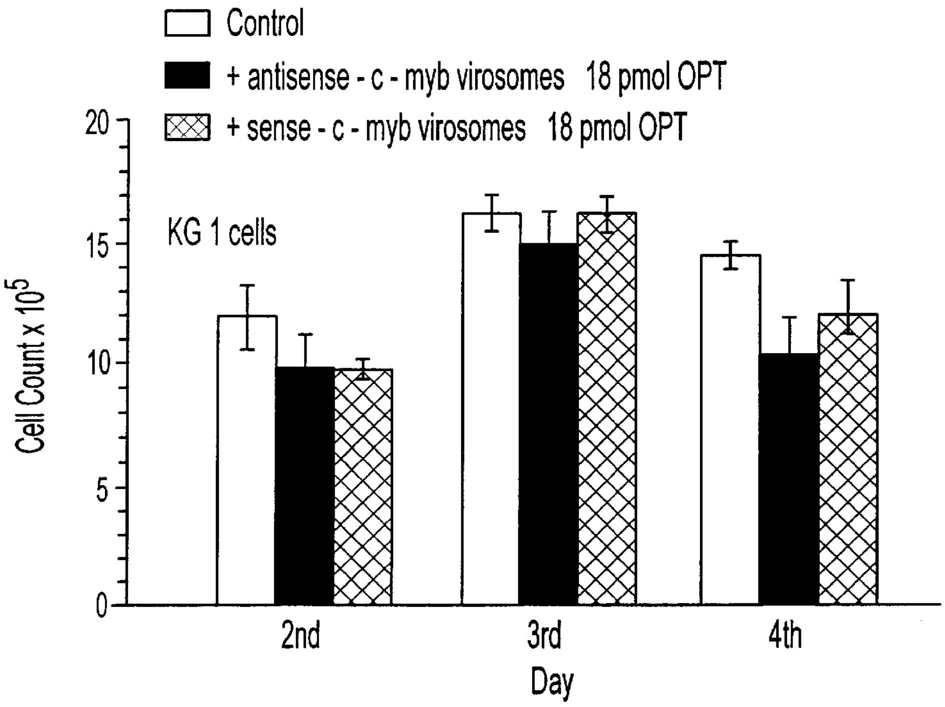
FIGS. 15, 16, 17: Cell growth of KG1 cells upon treatment with sense and antisense c-myb-DOTAP virosomes. Addition of 25, 50 or 100 $\mu$l of virosome solution containing 18, 36, or 72 pmol OPT, respectively. Values are the means±standard deviations of three experiments.
Figure 16:
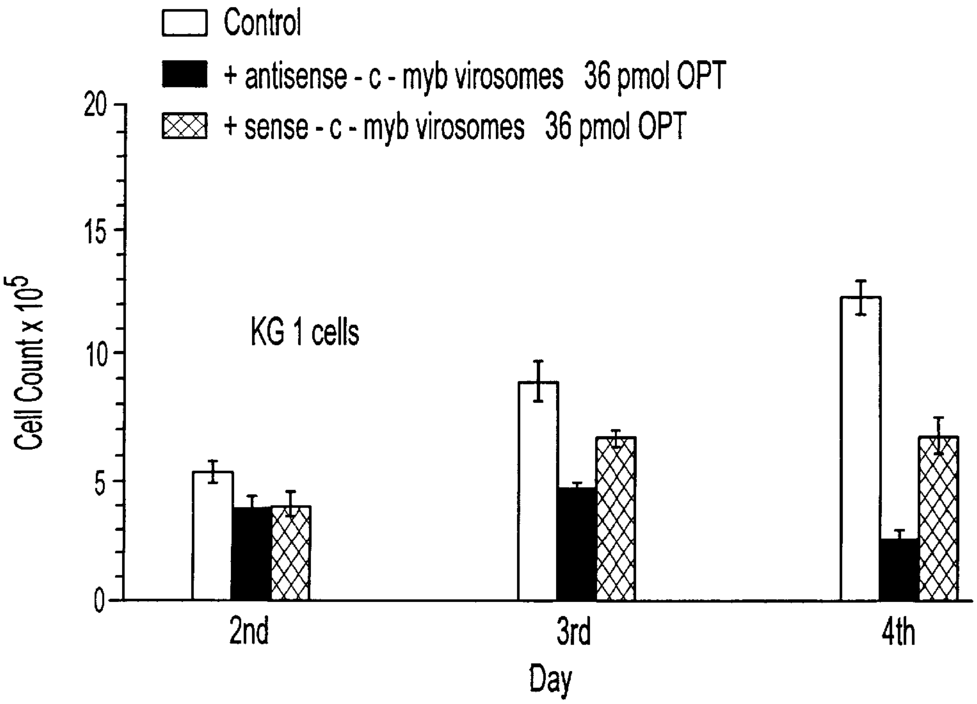
Figure 17:
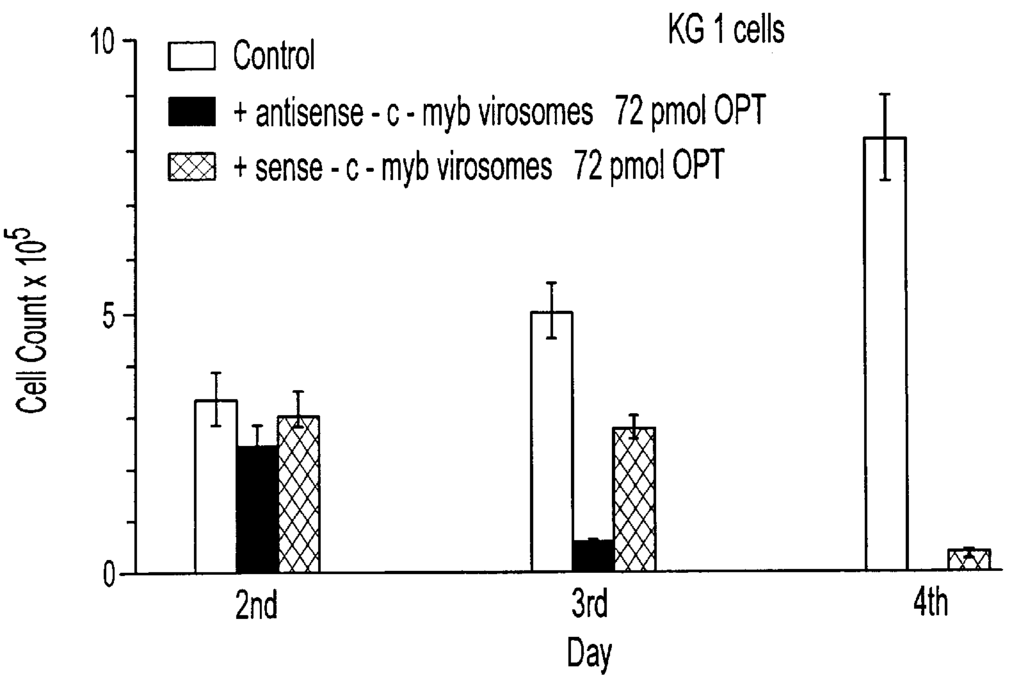
Figure 18:
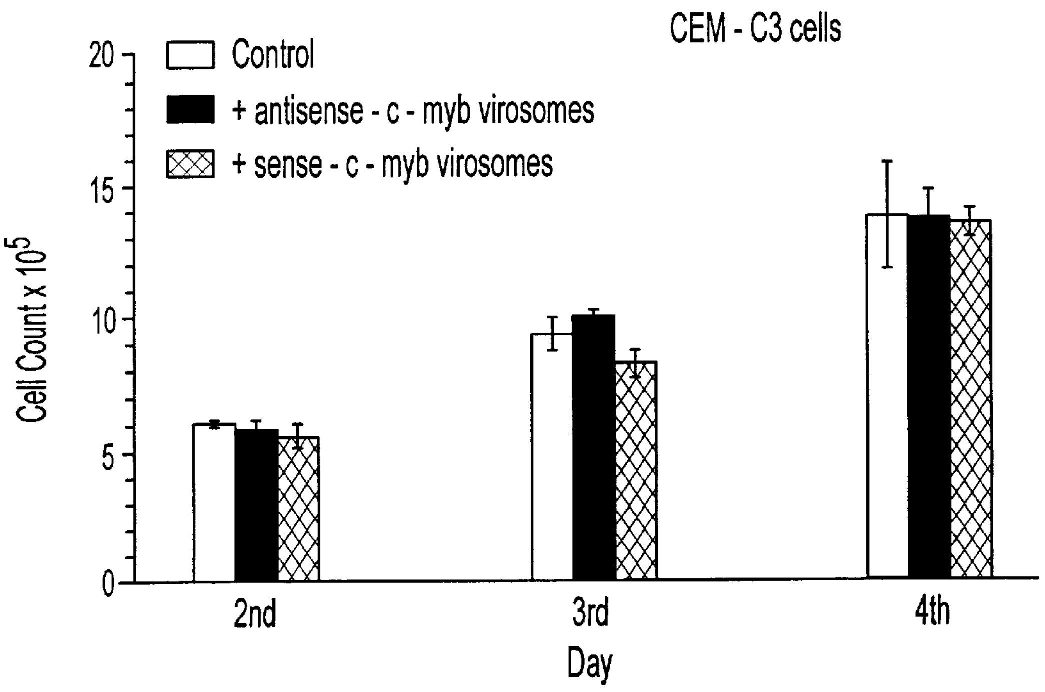
FIG. 18: Cell growth of CEM-C3 cells upon treatment with DOTAP-virosomes at the addition of 50 $\mu$l of sense and antisense c-myb virosome solution. Values are the means±standard deviations of three experiments.
Figure 19:
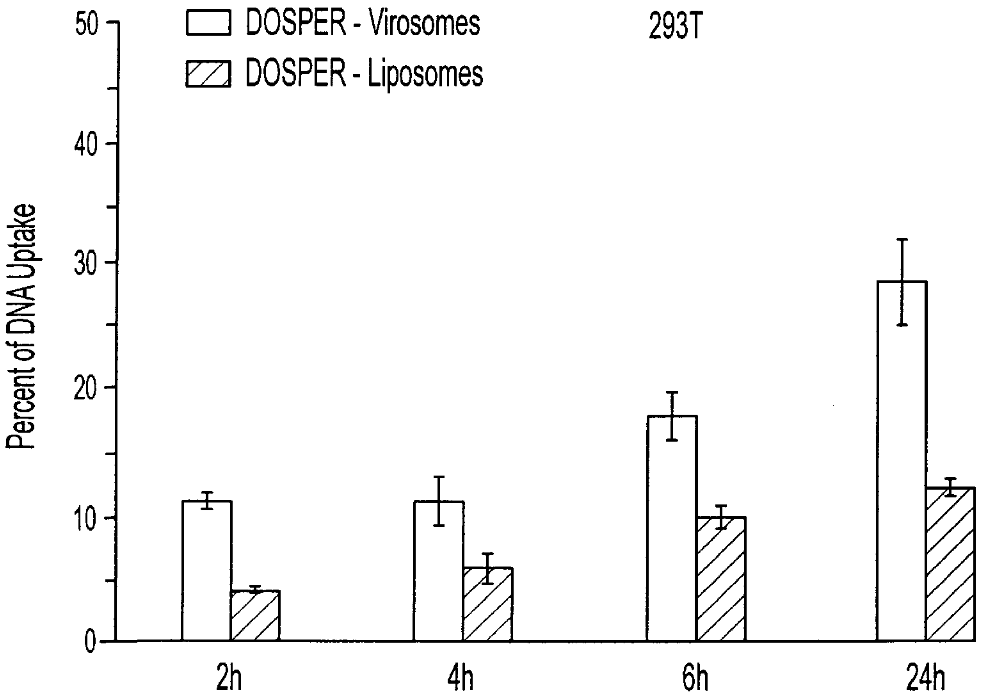
FIG. 19: Influence of time transfection on the amount of uptaken DNA-plasmid. $5\times10^5$ cells of human, transformed primary embryonal kidney cell line 293 T were transfected with DOSPER-virosomes and DOSPER-liposomes containing $^3$H-labeled plasmid pGreen Lantern.
Figure 20:
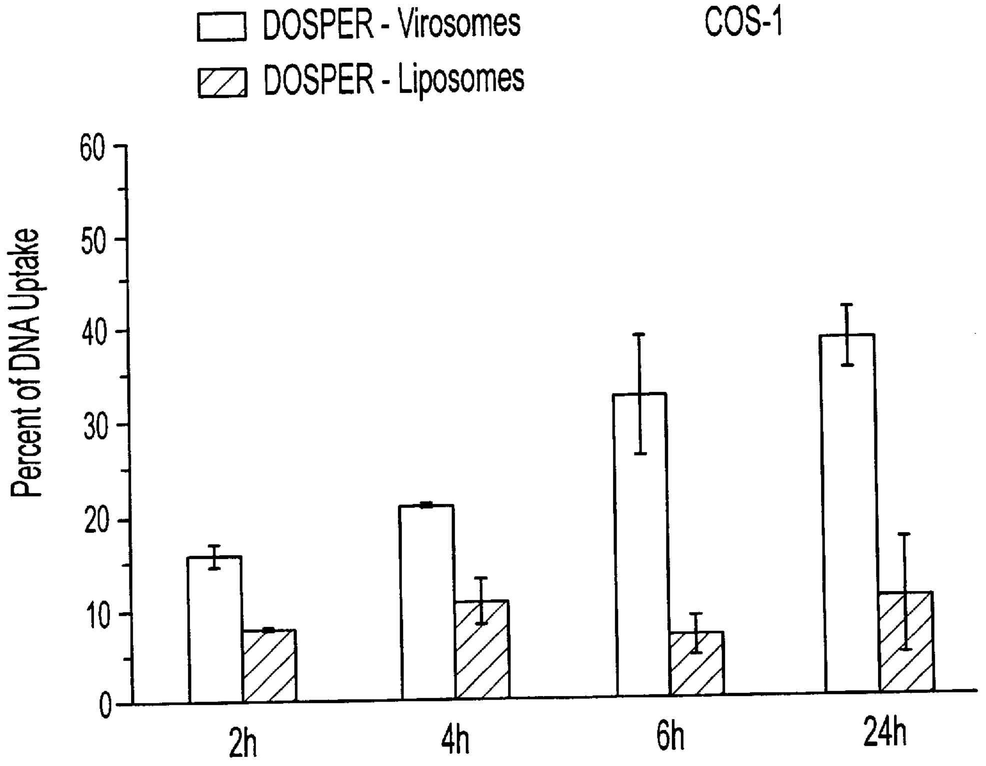
FIG. 20: Influence of time transfection on the amount of uptaken DNA-plasmid. $5\times10^5$ cells of monkey fibroblast cell line COS-1 were transfected with DOSPER-virosomes and DOSPER-lipsomes containing $^3$H-labeled plasmid pGreen Lantern.
Figure 21:
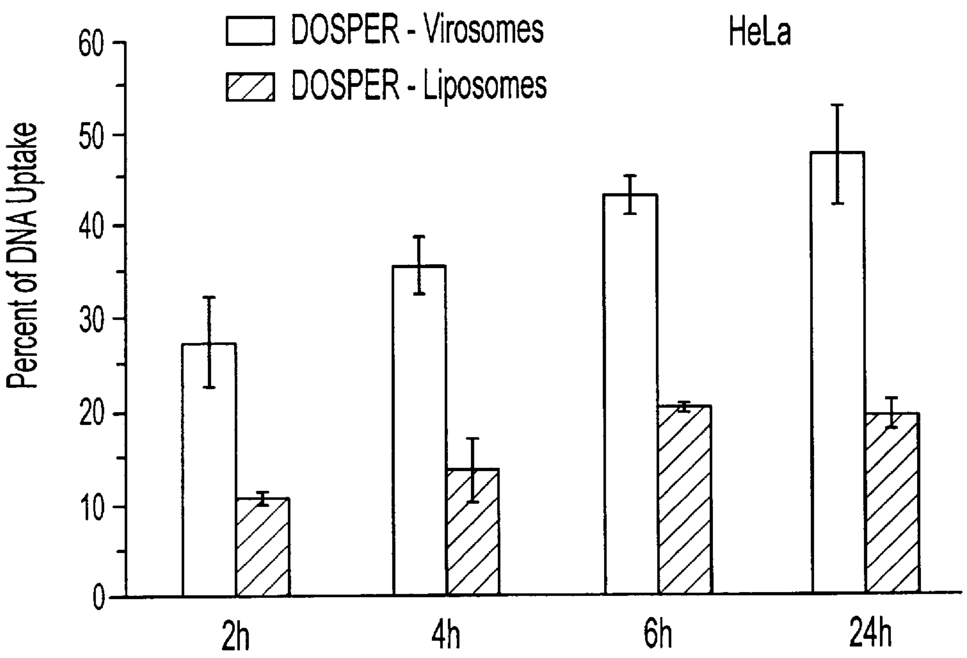
FIG. 21: Influence of time transfection on the amount of uptaken DNA-plasmid. $5\times10^5$ cells of human epithelioid carcinoma cell line HeLa were transfected with DOSPER-virosomes and DOSPER-liposomes containing $^3$H-labeled plasmid pGreen Lantern.
Figure 22:
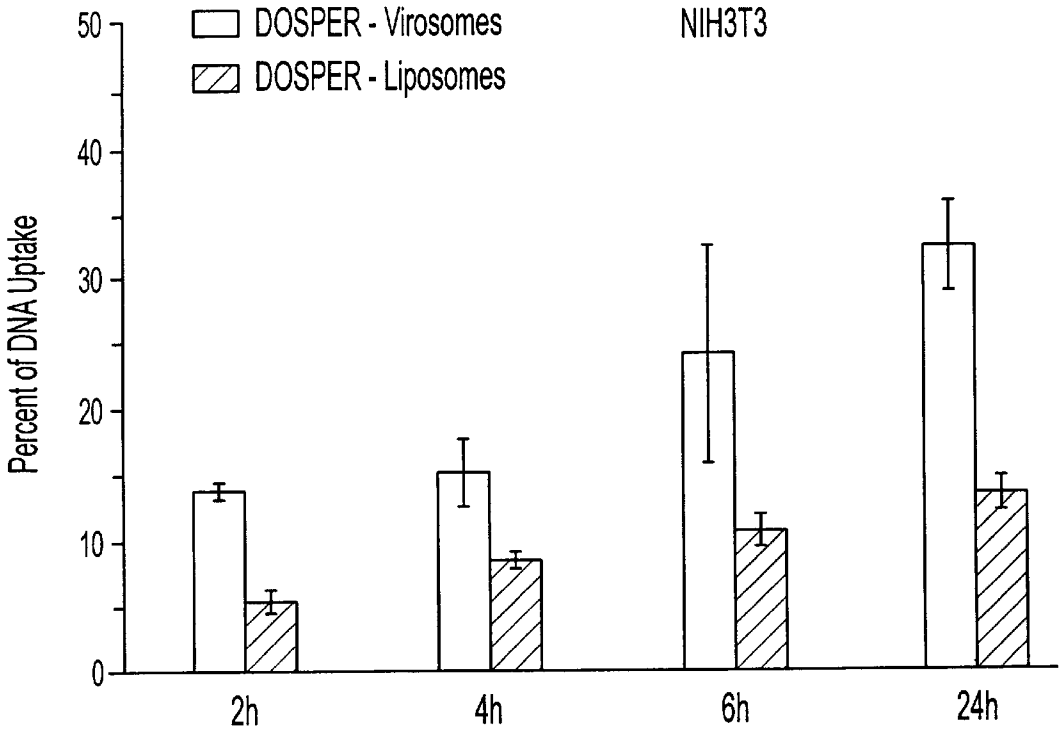
FIG. 22: Influence of time transfection on the amount of uptaken DNA-plasmid. $5\times10^5$ cells of mouse fibroblast cell line NIH3T3 were transfected with DOSPER-virosomes and DOSPER-liposomes containing $^3$H-labeled plasmid pGreen Lantern.
Figure 23:
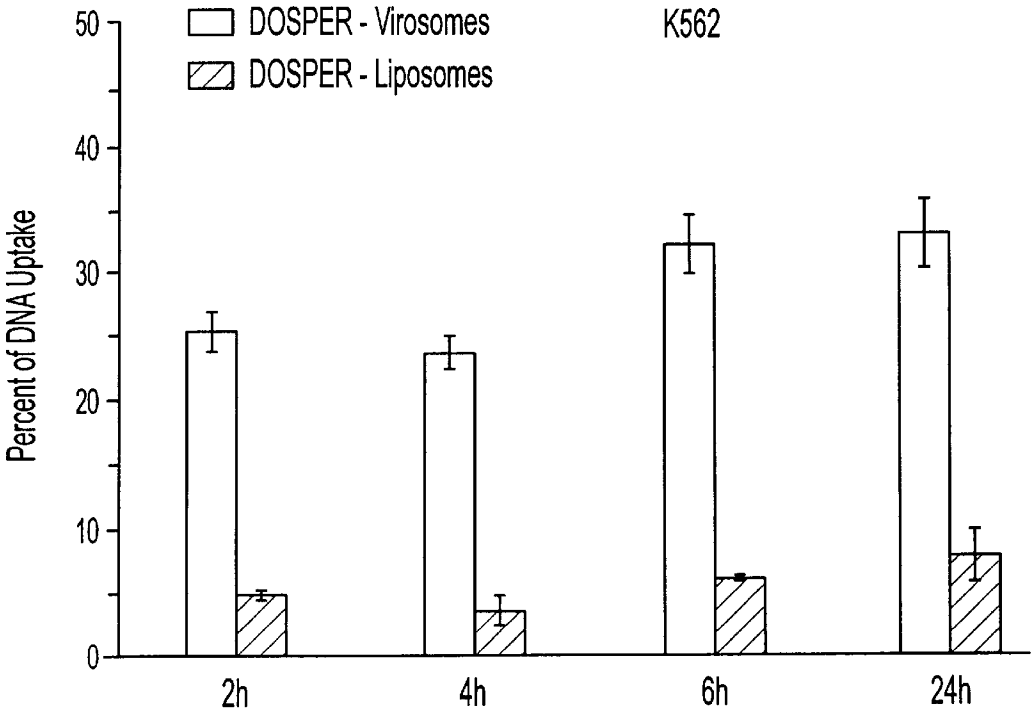
FIG. 23: Influence of time transfection on the amount of uptaken DNA-plasmid. $5\times10^5$ cells of human chronic myelogenous leukemia cell line K562 were transfected with DOSPER-virosomes and DOSPER-liposomes containing $^3$H-labeled plasmid pGreen Lantern.
Figure 24:
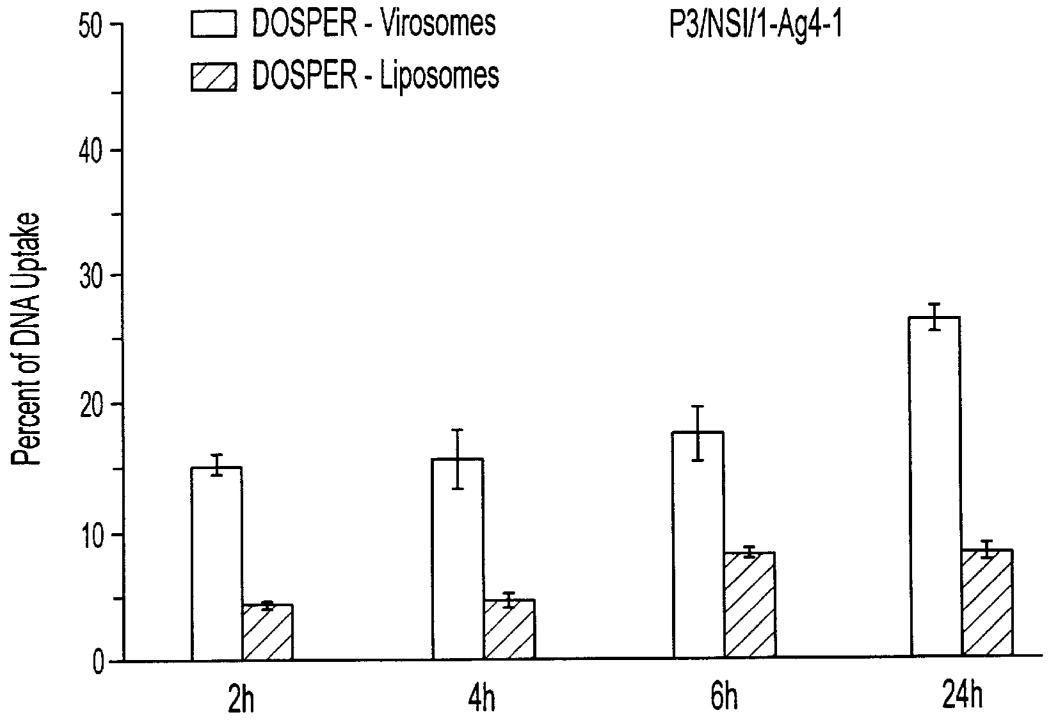
FIG. 24: Influence of time transfection on the amount of uptaken DNA-plasmid. $5\times10^5$ cells of mouse myeloma cell line P3 were transfected with DOSPER-virosomes and DOSPER-liposomes containing $^3$H-labeled plasmid pGreen Lantern.

Addition of 25 $\mu$l of sense and antisense c-myb virosomes had only marginal effects on the cell growth (FIG. 15). However, addition of 50 $\mu$l (FIG. 16) and 100 $\mu$l (FIG. 17) strongly inhibited the cell growth. Higher doses of sense c-myb virosomes also showed inhibitory effects. It is assumed that these effects were not elicited by the virosomal membrane, because CEM-C3 cells were not influenced by the same virosome preparations (FIG. 18).

EXAMPLE 8

DOSPER-Virosomes: Reagent for the Transfection of Eukaryotic Cells; Transfection of $^3$H-labeled Plasmid by DOSPER-Virosomes; a Comparison of DOSPER-Virosomes to DOSPER-Liposomes The plasmid pGEEN LANTERN™-I (GIBCOBRL) was produced in presence of $^3$H-methylthymidine. 33 μg of the labeled plasmid DNA were encapsulated into DOSPER-virosomes and 11.7 μg into DOSPER-liposomes.

The lipid bilayer of the DOSPER-virosomes consists of 25% of DOSPER and 75% of PC (phosphatidylcholine). It is impossible to produce DOSPER-virosomes with a 100% DOSPER bilayer. In particular, it has been found that if the concentration of DOSPER in the reaction mixture is more than, for example, 30%, virosomes may not form.

$5\times10^5$ cells of each cell type were incubated in 500 μl of medium either with 25 μl of plasmid-containing DOSPER-virosomes or DOSPER-liposomes solution for 2, 4, 6 and 24 h at 37° C. The added aliquots of DOSPER-virosomes and DOSPER-liposomes corresponded to a radioactivity of 26,500 dpm. After incubation, cells were washed, lysed and the radioactivity measured. The influence of time transfection on the amount of uptaken DNA-plasmid were evaluated with various cell lines, and the results are graphed in FIGS. 19–26. The Brief Description of the Figures above summarizes the cell lines in each of the Figures.

FIGS. 19–24 show clearly that DOSPER-virosomes are superior in transfection to DOSPER-liposomes for all cell types and for all incubation times. Longer incubation times of 6 and 24 h with DOSPER-liposomes only resulted in very minimal increases of DNA uptake, whereas longer incubation times with DOSPER-virosomes led to considerably higher DNA uptake. This result suggests that the HA-mediated uptake of virosomes is far more efficient than the uptake induced by DOSPER-liposomes without the help of any viral binding ligands to cell receptors. It is interesting that in the case of DOSPER-virosomes, incubation times of 6–24 h did not lead to a saturation of DNA incorporation but to a further increase of DNA uptake, an effect which may be due to a rapid replacement of membrane receptors after their removing by receptor-mediated endocytosis of the virosomes on the cell surface.

EXAMPLE 9

A Comparison of DOSPER-Virosomes to DOTAP-Virosomes

The same amount of $^3$H-labeled plasmid as described in Example 8 for DOSPER-virosomes was encapsulated into DOTAP-Virosomes. HeLa and K562 cells were incubated with DOTAP-Virosomes under the same conditions as described above in Example 8. The results are graphed in FIGS. 25 and 26.

Figure 25:
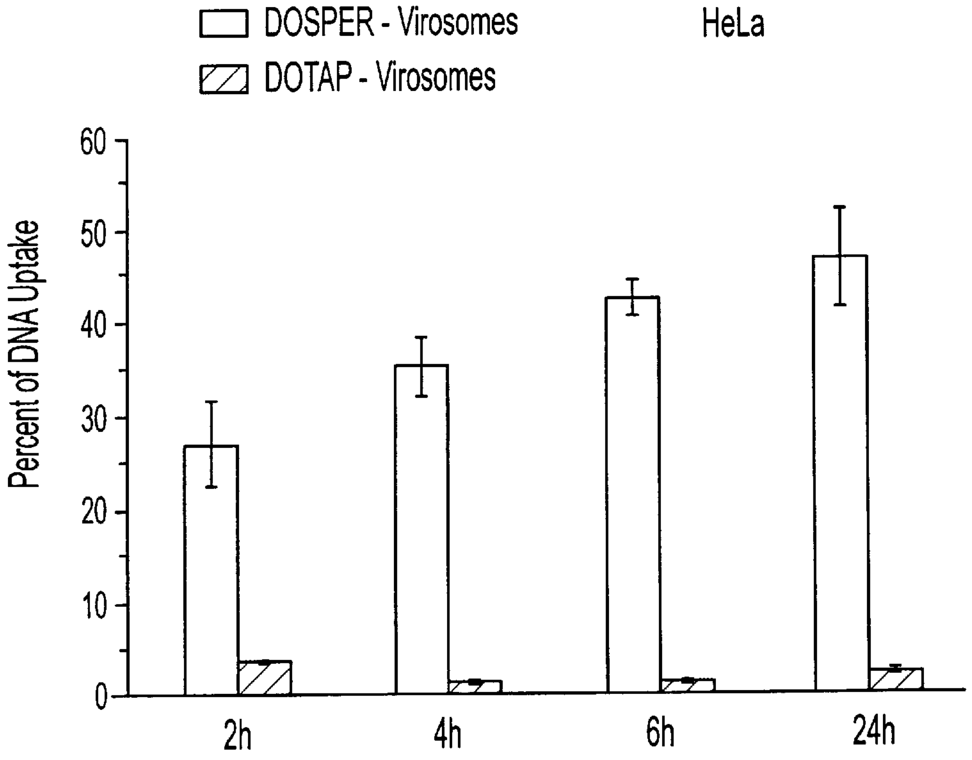
FIG. 25: Influence of time transfection on the amount of uptaken DNA-plasmid. $5\times10^5$ cells of human epithelioid carcinoma cell line HeLa were transfected with DOSPER-virosomes and DOTAP-virosomes containing $^3$H-labeled plasmid pGreen Lantern.
Figure 26:
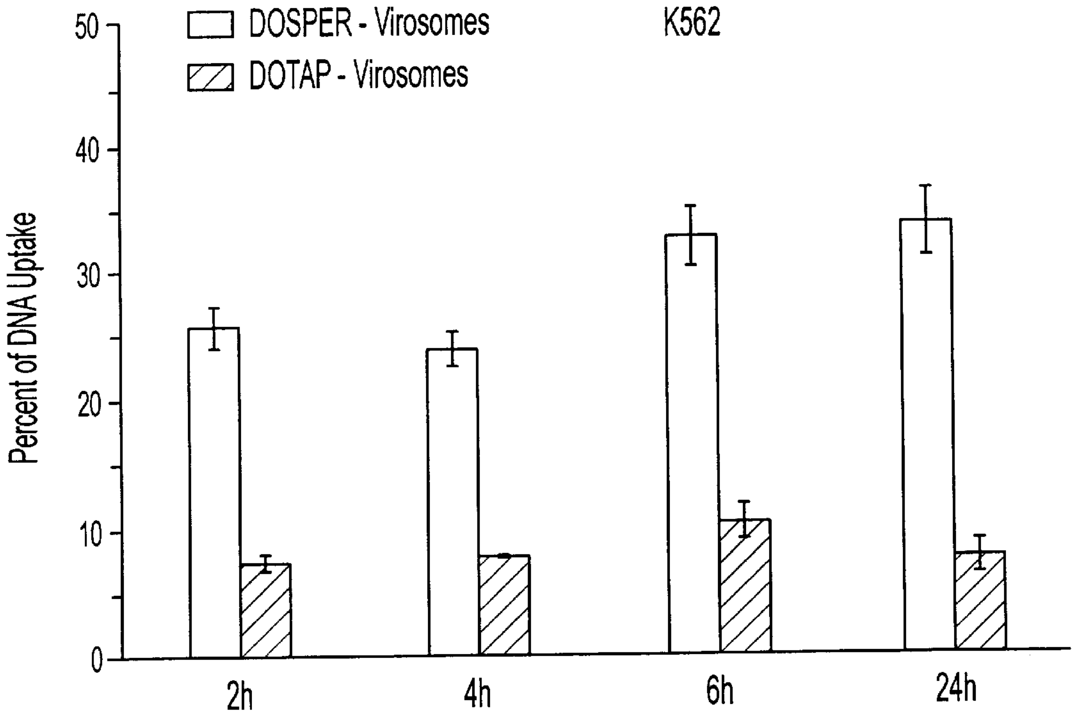
FIG. 26: Influence of time transfection on the amount of uptaken DNA-plasmid. $5\times10^5$ cells of human chronic myelogenous leukemia cell line K562 were transfected with DOSPER-virosomes and DOTAP-virosomes containing $^3$H-labeled plasmid pGreen Lantern.

The results in FIGS. 25 and 26 demonstrate that the transfection efficiency of DOTAP-virosomes is lower than that of DOSPER-virosomes. The reasons why are not clear. We suppose, without being bound by theory, that encapsulation of plasmid into virosomes containing DOSPER may lead to higher amounts of useful virosomes. In contrast, encapsulation of plasmid into DOTAP-virosomes may result in a high number of defective vesicles with low transfection potential. A second hypothesis would implicate an enhancing effect of DOSPER during binding of the virosomes to the cell membrane, a viewpoint we cannot exclude.

The results thus demonstrate that use of the polycationic lipid DOSPER exhibits surprisingly superior transfection efficiency compared to the most frequently used cationic lipid DOTAP.

Abbreviations used in the description

| | |
|---|---|
| 2'-OMe | 2'-O methyl |
| CALLA | common acute lymphoblastic leukemia antigen |
| CAT | chloramphenicol acteyltransferase |
| DOTAP | N-[(1,2,3-dioleoyloxy)-propyl]-N,N,N-trimethylammoniummethyl-sulfate |
| DOTMA | N-[(1,2,3-dioleoyloxy)propyl]-N,N,N-trimethylammonium chloride |
| FITC-OPT | fluorescein isothiocyanate-labeled oligodeoxyribonucleotide phosphorothioate |
| G418 | Geneticin ® disulfat (antibiotic G418) |
| HA | hemagglutinin |
| IL-6 | Interleukin 6 |
| MPB.PE | N-[4-(p-maleimido)-phenylbutyryl]-phosphatidylethanolamine ( = a crosslinker-phospholipid complex) |
| msc | mixed sequence control |
| NA | neuraminidase |
| Octyl-POE | n-octyl-oligo-oxyethylene |
| ODN | oligodeoxynucleotides |
| OEG | octaethyleneglycol monododecylether ($C_{12}E_8$) |
| OPT | oligodeoxyribonucleotide phosphorothioate(s) |
| PC | phosphatidylcholine |
| PE | phosphatidylethanolamine |
| PNA | peptide nucleic acid |
| SCLC | small cell lung cancer |
| SV40 | Simian virus 40 |

What is claimed is:

1. A lipid bilayer vesicle containing at least one desired drug or pharmaceutically active substance, said vesicle comprising:

(a) a membrane having a positive net charge and having phosphatidylethanolamine (PE) in combination with one or more other lipids comprising positively charged natural or synthetic lipids;

(b) at least one active fusion peptide that is a viral hemagglutinin, that is capable of causing the vesicles to be internalized by target cells through phagocytosis or endocytosis, and that exerts fusogenic activity at acidic pH within a range of pH5 to pH7, said hemagglutinin being attached directly or indirectly to said membrane;

(c) a bifunctional crosslinker linked to phosphatidylethanolamine (PE) of said membrane; and (d) at least one cell-specific marker linked via a sulfur of the cell-specific marker to the PE-bound crosslinker, said marker being a biologically active protein for binding to a receptor of target cells;

wherein the membrane comprises—based on total lipids—10% by weight or less of phosphatidylethanolamine, and 90% by weight or more of said other lipids comprising the positively charge lipids.

2. The vesicle according to claim 1, wherein the cell-specific marker is selected from the group consisting of an antibody, an antibody fragment, a cytokine and a growth factor.

3. The vesicle according to claim 1, wherein the positively charged lipids comprise at least one cationic or polycationic lipid selected from the group consisting of N-[(1,2,3-dioleoyloxy)propyl]-N,N,N-trimethylammonium chloride (DOTMA); N-[(1,2,3-dioleoyloxy)-propyl]-N,N,N-trimethylammoniummethylsulfate (DOTAP); N-t-butyl-N'-tetradecyl-3-tetradecylaminopropionamidine; 1,3-dipalmitoyl-2-phosphatidylethanolamidospermine (DPPES); dioctadecylamidoglycylspermine (DOGS); 2,3-dioleyloxy-N-[2(spermine-carboxamido)ethyl]-N,N-dimethyl-1-propaneaminiumtrifluoraoetate (DOSPA); 1,3-dioleoyloxy-2-(6-carboxy-spermyl)-propylamide (DOSPER); and N,N,N',N'-tetramethyl-N,N'-bis(2-hydroxyethyl)-2,3-dioleoyloxy-1,4-butanediammoniumiodide (THDOB).

4. The vesicle according to claim 1, wherein the desired drug or pharmaceutically active substance is a nucleic acid material.

5. The vesicle according to claim 1, wherein its diameter is in a range of 120–180 nm.

6. The vesicle according to claim 1, wherein the hemagglutinin is fusogenic at acidic pH within a range of pH7–pH5 and is derived from a virus selected from the group consisting of rhabdovirus, parainfluenza virus type III, Semliki Forest virus and togavirus.

7. The vesicle according to claim 3, wherein the membrane comprises 5 to 30% by weight, based on total lipids, of 1,3-dioleoyloxy-2-(6-carboxy-spermyl)-propylamide (DOSPER).

8. The vesicle according to claim 4, wherein said nucleic acid material contained in said vesicle is selected from the group consisting of short chain DNA or RNA, deoxyribonucleotides, oligodeoxyribonucleotides, oligodeoxyribonucleotide selenoates, oligodeoxyribonucleotide phosphorothioates, oligodeoxyribonucleotide phosphoramidates, oligodeoxyribonucleotide methylphosphonates, peptide nucleic acids, ribonucleotides, oligoribonucleotides, oligoribonucleotide phosphorothioates, 2'-OMe-oligoribonucleotide phosphates, 2'-OMe-oligoribonucleotide phosphorothioates, ribozymes, genes, plasmids and vectors.

9. The process according to claim 5, wherein the positively charged lipids comprise at least one cationic or polycationic lipid selected from the group consisting of N-[(1,2,3-dioleoyloxy)propyl]-N,N,N-trimethylammonium chloride (DOTMA); N-[(1,2,3-dioleoyloxy)-propyl]-N,N,N-trimethylammoniummethylsulfate (DOTAP); N-t-butyl-N'-tetradecyl-3-tetradecylaminopropionamidine; 1,3-dipalmitoyl-2-phosphatidylethanolamidospermine (DPPES); dioctadecylamidoglycylspermine (DOGS); 2,3-dioleyloxy-N-[2(spermine-carboxamido)ethyl]-N,N-dimethyl-1-propaneminiumtrifluoroacetate (DOSPA); 1,3-dioleoyloxy-2-(6-carboxy-spermyl)-propylamide (DOSPER); and N,N,N',N'-tetramethyl-N,N'-bis(2-hydroxyethyl)-2,3-dioleoyloxy-1,4-butanediammoniumiodide (THDOB).

10. The process according to claim 5, wherein the positively charged lipids comprise 5 to 30% by weight of 1,3-dioeoyloxy-2-(6-carboxy-spermyl)-propylamide (DOSPER), based on total lipids.

11. A process for the manufacture of a lipid bilayer vesicle having a membrane that contains natural or synthetic lipids having a positive net charge together with phosphatidylethanolamine, at least one functionally active viral fusogenic peptide integrated in or covalently linked to the membrane, at least one cell-specific marker attached to the membrane, and a desired nucleic acid material, comprising the steps of (a) dissolving purified virus with a non-ionic detergent solution and separating therefrom a fraction containing hemagglutinin;

(b) preparing conjugate molecule complexes consisting of phosphatidylethanolamine (PE), a bifunctional crosslinker, and a cell-specific marker in a way such that the bifunctional crosslinker with one binding site links to an amino group of PE and with another one to a thiol group of the cell-specific marker, and removing unconjugated material;

(c) preparing a solution containing:

a buffered non-ionic detergent; viral hemagglutinin obtained in step (a); natural or synthetic lipids other than PE comprising lipids that have a positive net charge; and at least one cell-specific marker in the form of said conjugate molecule complexes of (b) of PE/crosslinker/marker;

(d) adjusting the lipid concentrations to—based on total lipids—10% by weight or less of phosphatidylethanolamine and to 90% by weight or more of said natural or synthetic lipids other than PE comprising lipids that have a positive net charge;

(e) removing the detergent by dialysis or by treating the solution with microcarrier beads, resulting in the formation of positively charged targeted virosomes; and (f) incorporating into the virosomes a quantity of a desired nucleic acid material.

12. The process according to claim 11, wherein said lipids other than PE include phosphatidylcholine.

13. The process according to claim 11, wherein said microcarrier beads are polystyrene beads having a net mesh size of 20–50 (0.84–0.30 nm).

14. The process according to claim 11, wherein incorporation of nucleic acid material into the virosomes is accomplished by adding to the virosomes resulting from step (e) the desired nucleic acid material, sonicating the mixture to integrate the material into the vesicles, and removing non-integrated material.

15. The process according to claim 11, wherein incorporation of nucleic acid material into the virosomes is accomplished by adding to the virosomes resulting from step (e) positively charged liposomes containing the desired nucleic acid material and sonicating the mixture to fuse the liposomes with the virosomes to integrate the nucleic acid material into the virosomes.

16. The process according to claim 11, wherein the weight ratio of hemagglutinin to total membrane lipids is adjusted to approximately 1 (mg/mg) or less.

17. The process according to claim 11, wherein the cell-specific marker is selected from the group consisting of an antibody, an antibody fragment, a cytokine and a growth factor.

18. The process according to claim 11, wherein the desired nucleic acid material is selected from the group consisting of short chain DNA or RNA, deoxyribonucleotides, oligodeoxyribonucleotides, oligodeoxyribonucleotide selenoates, oligodeoxyribonucleotide phosphorothioates, oligodeoxyribonucleotide phosphoramidates, oligodeoxyribonucleotide methylphosphonates, peptide nucleic acids, ribonucleotides, oligoribonucleotides, oligoribonucleotide phosphorothioates, 2'-OMe-oligoribonucleotide phosphates, 2'-OMe-oligoribonucleotide phosphorothioates, ribozymes, genes, plasmids and vectors.

19. The process according to claim 11, wherein the non-ionic detergent solution comprises $C_{12}E_8$ (octaethyleneglycol monododecylether) or n-octyl-oligooxyethylene.

20. The process according to claim 11, wherein the crosslinking agent is a heterobifunctional organic molecule having at least one maleimido and at least one carboxyl group.

21. The process according to claim 11, wherein in step (b), unconjugated material is removed by affinity chromatography using an agarose matrix.

22. A lipid bilayer vesicle obtained by the process of claim 11.

23. The process according to claim 14, wherein the non-integrated material is removed by gel filtration.

24. The process according to claim 17, wherein the cell-specific marker is a Fab' or $F(ab')_2$ fragment and is applied in a weight ratio of hemagglutinin to Fab' or $F(ab')_2$ fragment of about 2:1.

25. The process according to claim 20, wherein the crosslinking agent is selected from the group consisting of bis-N-succinimidyl derivatives and photactivatable succinimidyl derivatives.

26. A method for delivering a desired nucleic acid material to resting or proliferating target cells, comprising, incubating said target cells in vitro in the presence of positively charged lipid bilayer vesicles as defined in claim 1 wherein the nucleic acid material is delivered to the cell.

27. The method according to claim 26, wherein the target cells are selected from the group consisting of cancer cells, leukemic cells and virally infected cells, and metabolic or proliferative activity of said target cells is reduced upon incubation in the presence of the positively charged lipid bilayer vesicles.

28. The method according to claim 26, wherein said nucleic acid material comprises at least one antisense oligonucleotide.

29. The method according to claim 28, wherein the antisense oligonucleotide is targeting protooncogene or oncogene encoded mRNA.

30. A lipid bilayer vesicle that contains at least one desired drug or pharmaceutically active substance and that further comprises:

(a) a membrane that has a positive net charge and comprises 5 to 30% by weight, based on total lipids, of 1,3-dioleoyloxy-2-(6-carboxy-spermyl)-propylamide (DOSPER), together with other lipids; and (b) at least one active fusion peptide that is a non-Sendai viral hemagglutinin that causes the vesicles to be internalized by target cells through phagocytosis or endocytosis.

31. The vesicle according to claim 30, wherein the other lipids comprise phosphatidylcholine.

32. The vesicle according to claim 30, wherein the desired drug or pharmaceutically active substance is a nucleic acid material.

33. The vesicle according to claim 30, wherein the vesicle has a diameter in a range of 120–180 nm.

34. A method for delivering a desired nucleic acid material to resting or proliferating target cells in vitro, comprising incubating said target cells in the presence of positively charged lipid bilayer vesicles as defined in claim 30 wherein the nucleic acid material is delivered to the cell.

35. The vesicle according to claim 31, wherein the vesicle has a diameter in a range of 120–180 nm.

36. The vesicle according to claim 32, wherein the nucleic acid material is selected from the group consisting of short chain DNA or RNA, deoxyribonucleotides, oligodeoxyribonucleotides, oligodeoxyribonucleotide selenoates, oligodeoxyribonucleotide phosphorothioates, oligodeoxyribonucleotide phosphoramidates, oligodeoxyribonucleotide methylphosphonates, peptide nucleic acids, ribonucleotides, oligoribonucleotides, oligoribonucleotide phosphorothioates, 2'-Ome-oligoribonucleotide phosphates, 2'-Ome-oligoribonucleotide phosphorothioates, ribozymes, genes, plasmids and vectors.

37. The vesicle according to claim 32, wherein the vesicle has a diameter in a range of 120–180 nm.

38. The method according to claim 34, wherein the target cells are selected from the group consisting of cancer cells, leukemic cells and virally infected cells, and metabolic or proliferative activity of said target cells is reduced upon incubation in the presence of the positively charged lipid bilayer vesicles.

39. The method according to claim 34, wherein said nucleic acid material comprises at least one antisense oligonucleotide.

40. The vesicle according to claim 36, wherein the vesicle has a diameter in a range of 120–180 nm.

41. The method according to claim 39, wherein the antisense oligonucleotide is targeting protooncogene or oncogene encoded mRNA.

* * * * *

UNITED STATES PATENT AND TRADEMARK OFFICE

CERTIFICATE OF CORRECTION

PATENT NO. : 6,210,708 B1
DATED : April 4, 2001
INVENTOR(S) : Ernst Rudolf Walti, Reinhard Gluck and Peter Klein It is certified that error appears in the above-identified patent and that said Letters Patent is hereby corrected as shown below:

Please correct claims 9 and 10 as follow:
Claim 9,
Line 1, change "claim 5" to -- claim 11 --.

Claim 10,
Line 1, change "claim 5" to -- claim 11 --.

Signed and Sealed this

Eighteenth Day of December, 2001

Attest:

JAMES E. ROGAN
*Director of the United States Patent and Trademark Office*

*Attesting Officer*